(12) United States Patent
Chakrabartty et al.

(10) Patent No.: US 7,794,692 B2
(45) Date of Patent: Sep. 14, 2010

(54) METHODS AND COMPOSITIONS FOR DETECTING AMYOTROPHIC LATERAL SCLEROSIS

(75) Inventors: Avijit Chakrabartty, Vaughan (CA); Neil R. Cashman, Vancouver (CA); Rishi Rakhit, Toronto (CA)

(73) Assignees: Amorfix Life Sciences Ltd., Toronto, Ontario; University Health Network, Toronto, Ontario ( * ) Notice: Subject to any disclaimer, the term of this patent is extended or adjusted under 35 U.S.C. 154(b) by 264 days.

(21) Appl. No.: 11/565,967

(22) Filed: Dec. 1, 2006

(65) Prior Publication Data

US 2008/0132685 A1 Jun. 5, 2008

Related U.S. Application Data

(60) Provisional application No. 60/741,462, filed on Dec. 2, 2005.

(51) Int. Cl.
*A61K 49/00* (2006.01)
*G01N 33/53* (2006.01)
*G01N 33/50* (2006.01)

(52) U.S. Cl. .................... 424/9.1; 435/7.95; 424/139.1

(58) Field of Classification Search ........................ None
See application file for complete search history.

(56) References Cited

U.S. PATENT DOCUMENTS

| | | | |
|---|---|---|---|
| 4,806,627 A | 2/1989 | Wisniewski et al. |
| 4,910,133 A | 3/1990 | Uda |
| 4,940,659 A | 7/1990 | Warrington |
| 5,834,457 A | 11/1998 | Bredesen |
| 5,849,290 A | 12/1998 | Brown |
| 6,270,954 B1 | 8/2001 | Welch |
| 6,406,864 B2 | 6/2002 | Prusiner |
| 6,541,195 B2 | 4/2003 | Welch |
| 6,677,125 B2 | 1/2004 | Prusiner |
| 6,743,771 B2 | 6/2004 | Douglas |
| 6,765,088 B1 | 7/2004 | Korth et al. |
| 7,041,807 B1 | 5/2006 | Cashman |
| 7,439,324 B2 | 10/2008 | Cashman |
| 2002/0123072 A1 | 9/2002 | Prusiner et al. |
| 2003/0022243 A1 | 1/2003 | Kondejewski et al. |
| 2006/0194821 A1 | 8/2006 | Lansbury |
| 2006/0211079 A1 | 9/2006 | Hazen et al. |
| 2006/0280733 A1 | 12/2006 | Kayed |
| 2007/0003977 A1 | 1/2007 | Cashman et al. |
| 2007/0292410 A1 | 12/2007 | Cashman et al. |
| 2008/0206251 A1 | 8/2008 | Cashman et al. |
| 2009/0098151 A1 | 4/2009 | Cashman et al. |

FOREIGN PATENT DOCUMENTS

| | | |
|---|---|---|
| CA | 2408762 | 4/2003 |
| CA | 2452946 | 6/2004 |
| WO | WO 00/12718 | 3/2000 |
| WO | WO00/22438 A1 | 4/2000 |
| WO | WO00/78344 A1 | 12/2000 |
| WO | WO01/06989 A2 | 2/2001 |
| WO | WO 2004/024090 | 3/2004 |
| WO | WO 2005/019828 | 3/2005 |
| WO | WO 2005/077040 | 8/2005 |
| WO | WO 2007/067900 | 6/2007 |

OTHER PUBLICATIONS

Johnston et al., PNAS, 97(23):12571-12576, Nov. 2000.*
Kunst et al., Nature Genetics, 15:91-94, 1997.*
Watanabe et al., PLoS ONE, 3(10): e3497, Oct. 2008.*
Jacobsson et al., Brain, 124:1461-1466, 2001.*
Liu et al., Ann Neurol., 66:75-80, 2009.*
Pardo, Carlos, et al. "Superoxide dismutase is an abundant component in cell bodies, dendrites, and axons of motor neurons and in a subset of other neurons", Proc. Natl. Acad. Sci., Feb. 1995, vol. 92, pp. 954-958.
Kayed, R. et al.; Common Structure of Soluble Amyloid Oligomers Implies Common Mechanism of Pathogenesis; Science, Apr. 18, 2003, p. 486-489, vol. 300; AAAS, New York, USA.
Rakhit, R. et al.; Monomeric Cu,Zn-superoxide Dismutase Is a Common Misfolding Intermediate in the Oxidation Models of Sporadic and Familial ALS; JBC, Apr. 9, 2004, p. 15499-15504, vol. 279, No. 15; ASBMB, Bethesda, USA.
Paramithiotis, E. et al.; A prion protein epitope selective for the pathologically misfolded conformation; Nature Medicine, Jul. 2003, vol. 9, No. 7; NPG, London, UK.
Kim, J.S.M. and Cashman, N.R.; Non-Specific Binding of Aggregated SOD1 to Antibodies. Abstract for Poster Presentation presented at the 15th International Symposium on ALS/MND, Dec. 2-4, 2004, Philadelphia, U.S.A. and published in ALS and other Motor Neuron Disorders 2004 (suppl 2) pp. 83-84 (Abstract p41).
Chakrabartty, Avijit.; Oxidation-induced misfolding monomerization and aggregation of SOD1 and its role in ALS, Slides and abstract, presented at the 15th International Symposium on ALS/MND, Dec. 2-4, 2004, Philadelphia, U.S.A. and abstract published in ALS and other Motor Neuron Disorders 2004 (suppl 2) 48-49 (Abstract c72.).
Deng, et al.: Amyotrophic lateral sclerosis and structural defects in Cu,Zn superoxide dismutase; Science, Aug. 20, 1993, pp. 1047-1051, vol. 261. AAAS, New York, U.S.A.
Rakhit, R., et al.; Oxidation-induced misfolding and aggregation of superoxide dismutase and its implications for amyotrophic lateral sclerosis. J Biol Chem. Dec. 6, 2002, pp. 47551-47556, vol. 277, No. 49. ASBMB, Bethesda, U.S.A.

(Continued)

*Primary Examiner*—John D. Ulm
*Assistant Examiner*—Stacey MacFarlane
(74) *Attorney, Agent, or Firm*—Bereskin & Parr LLP; Noel Courage; Carmela DeLuca

(57) ABSTRACT

The invention provides binding proteins that bind to misfolded or monomeric SOD1, and not to native homodimeric SOD1. The invention also includes methods of diagnosing, detecting or monitoring amyotrophic lateral sclerosis in a subject. In addition, the invention provides methods of identifying substances for the treatment or prevention of amyotrophic lateral sclerosis and kits using the binding proteins of the invention.

8 Claims, 14 Drawing Sheets

OTHER PUBLICATIONS

Khare, et al.; Sequence and structural determinants of Cu, Zn superoxide dismutase aggregation. Proteins. Nov. 15, 2005, pp. 617-632, vol. 61, No. 3. Wiley-Liss, New York, U.S.A.

Elam J.S., et al.; Amyloid-like filaments and water-filled nanotubes formed by SOD1 mutant proteins linked to familial ALS. Nature Struct. Biol. Jun. 2003, pp. 461-467, vol. 10, No. 6. Nature Pub. Co., New York, U.S.A.

Jonsson, et al.; Minute quantities of misfolded mutant superoxide dismutase-1 cause amyotrophic lateral sclerosis. Brain. Jan. 2004, pp. 73-88, vol. 127., Oxford University Press, England.

Urushitani, et al.; Chromogranin-mediated secretion of mutant superoxide dismutase proteins linked to amyotrophic lateral sclerosis. Nature Neurosci. Jan. 2003, pp. 108-118, vol. 9, No. 1. Nature Publishing Group, New York, U.S.A.

Sendtner, M.; Damaging secretions: chromogranins team up with mutant SOD1. Nature Neurosci. Jan. 2006, pp. 12-14, vol. 9, No. 1. Nature Publishing Group, New York, U.S.A.

McCaffrey, P.; SOD1 mutant protein gets loose in ALS. Lancet Neurology, Feb. 2006, p. 119, vol. 5, No. 2. Lancet Publishing Gropup, New York, U.S.A.

Griffin, et al; Isomorphic recruitment of superoxide dismutase in amyotrophic lateral sclerosis, Poster presented at the 13$^{th}$ International Symposium on ALS/MND, Nov. 2002.

Soto, C.; Diagnosing prion diseases: needs, challenges and hopes, Nature Rev. Microbial., Oct. 2004, pp. 809-819, vol. 2, No. 10.

Bolton, et al.; Molecular location of a Species-specific epitope on the hampster scrapie agent protein, J. of Virology, Jul. 1991, pp. 3667-3675, vol. 65, No. 7.

Safar, et al. ; Measuring prions causing bovine spongiform enecephalopathy or chronic wasting disease bu immunoassays and transgenic mice, Natural Biotechnol. Nov. 2002, pp. 1147-1150, vol. 20, No. 11.

Hsueh-Ning Liu et al., Lack of Evidence of Monomer/Misfolded Superoxide Dismutase-1 in Sporadic Amyotrophic Lateral Sclerosis, Annals of Neurology, vol. 66, No. 1, pp. 75-80, Jul. 2009.

S. A. Ezzi et al., Wild-type superoxide dismutase acquires binding and toxic properties of ALS-linked mutant forms through oxidation, J Neurochem, Jul. 2007; 102(1):170-8. Epub Mar. 29, 2007.

J. Brettschneider et al., Axonal damage markers in cerebrospinal fluid are increased in ALS, Neurology, Mar. 28, 2006; 66(6): 852-6.

Makoto Urushitani et al., The endoplasmic reticulum-Golgi pathway is a target for translocation and aggregation of mutant superoxide dismutase linked to ALS, The FASEB Journal, vol. 22, pp. 2476-2487, Jul. 2008.

Deng H.X. et al., Conversion to the amyotrophic lateral sclerosis phenotype is associated with intermolecular linked insoluble aggregates of SOD1 in mitochondria. Proc. Natl. Acad. Sci., May 2, 2006, pp. 7142-7147, vol. 103, No. 18 National Academy of Sciences, D.C., U.S.A.

Furukaway Y. et. al., Disulfide cross-linked protein represents a significant fraction of ALS-associated Cu, Zn-superoxide dismutase aggregates in spinal cords of model mice. Proc. Natl. Acad. Sci., May 2, 2006, pp. 7148-7153, vol. 103, No. 18 National Academy of Sciences, D.C., U.S.A.

Lehto et al., Peroxynitrite as a probe for the structure of normal and misfolded prion protein, poster and abstract presented at the Society for Neuroscience 32nd Annual Meeting, Nov. 2-7, 2002, Orlando, Florida.

Kalnine N. et al., UnitProt Accession No. Q6NR8. Superoxide dismutase 1. [online] May 10, 2005.

Gelinas D.S. et al., Immunotherapy for Alzheimer's disease. Proceedings for the National Academy of Sciences of the United States of America. Oct. 5, 2004. vol. 101, suppl. 2, pp. 14657-14662.

Griffin and Cashman, Progress in prion vaccines and immunotherapies. Expert Opinion on Biological Therapies. Jan. 6, 2005. vol. 5, No. 1, pp. 97-100.

Burgess et al., Possible Dissociation of the Herapin-binding and Mitogenic Activities of Heparin-bidning (Acid Fibroplast) Growth-Factor-1 from Its Receptor-binding Activities by Site-directed Mutagenesis of a Single Lysine Residue, The Journalof. Cell Biioology 1990, 111:2129-2138.

Bowie et al., Deciphering the Message in Protein Sequences: Tolerance to Amino Acid Substitutions, Science, 1990, 247:1306-1310.

Pawson et al., Assembly of Cell Regulatory Systems Through Protein Interaction Domains, 2003, Science 300:445-452.

Kim et al.; Aggregation of Alfa-Synclucein induced by the Cu,Zn-Superoxide dismutase and hydrogen peroxide system, Free Rad Biol. Med. 2002. 32:544-550.

Session 7A protein folding and degradation effects: Function of the proteasome in cell regulation and neuromuscular disease, Amytrophic Lateral Sclerosis, 2005, 6: 33-35.

Valentine J.S. et al, Copper-Zinc Superoxide dismutase and amytrophoc lateral sclerosis, Annual Rev. Biochem. 2005, 74: 563-593.

Goodall E.F. et al., Amyotrophic lateral sclerosis (motor neuron disease): proposed mechanism and pathways to treatment, Expert Reviews in Molecular Reviews, 2006, 8(11): 1-24.

Julien, Mouse models of amyotrophic lateral sclerosis, Elsevier Disease Models, 2006, 3(4): 331-339.

Le Pecheur et al., FEBS Letters, 579(17): 3613-3618, 2005.

Bruijn L. et al., ALS-linked SOD1 mutant G85R mediates damage to astrocytes and promotes rapidly progressive disease with SOD1-containing inclusions, Neuron 1997, vol. 18(2):327-338.

Liu H.S. et al., P139 Abstract, An immunization strategy for treating amyotrphic lateral sclerosis that targets misfolded SOD1, Amyotrophic Lateral Sclerosis 2007 (Suppl 1); 8:140-155, p. 150.

Kerman A, et al., P163 Investigation of Cu/Zn superoxide dismutase misfolding and aggregation in ALS using conformation-specific antibodies. Amyotrophic Lateral Sclerosis 2007 (Suppl 1); 8:156-177, Abstract p. 164.

Rakhit R, et al. An Immunological epitope selective for pathological monomer-misfolded SOD1 in ALS, Nature medicine Jun. 2007, vol. 13, No. 6, pp. 754-759.

Kerman, A., Amyotrophic lateral sclerosis is a non-amyloid disease in which extensive misfolding of SOD1 is unique to the familial form. Acta Neuropathol, Jan. 2010, 119:335-344.

Choi, et al.; Oxidative modifications and Aggregation of Cu, Zn-superoxide dismutase associated with Alzheimer and Parkinson diseases. The Journal of Biological Chemistry. Mar. 25, 2005. pp. 11648-11655, vol. 280, No. 12. Published online Jan. 19, 2005.

\* cited by examiner

METHODS AND COMPOSITIONS FOR DETECTING AMYOTROPHIC LATERAL SCLEROSIS

This application claims the benefit under 35 USC §119(e) from U.S. Provisional patent application Ser. No. 60/741,462, filed Dec. 2, 2005, which is incorporated herein by reference in its entirety.

FIELD OF THE INVENTION

The invention relates to methods and compositions for detecting and monitoring amyotrophic lateral sclerosis in a subject.

BACKGROUND OF THE INVENTION

Amyotrophic lateral sclerosis (ALS) is a devastating motor neuron disease resulting in paralysis and death usually within 3-5 years of diagnosis[1]. The landmark discovery in 1993 of pathogenic mutations of Cu/Zn superoxide dismutase (SOD1) in a subset of familial ALS has spurred research into the mechanism of SOD1-related ALS (SOD1-ALS)[2]. A combination of genetic and biophysical techniques has shown that SOD1 point-mutations produce a toxic gain-of-function, the exact nature of which remains unresolved[1]. One proposed mechanism is that misfolding and aggregation of the mutant SOD1 protein underlies toxicity. Inclusion bodies immunoreactive for SOD1 are present in human cases of SOD1-ALS and in transgenic ALS models[3]. The mechanism(s) by which in vivo misfolded and aggregated SOD1 exhibits toxicity have been proposed to involve overwhelming the protein-folding chaperone system[4,5], inhibition of proteasomes[6], or aberrant interactions with mitochondrial proteins such as Tom20[7] or Bcl-2[8]. Another proposed gain-of-function for mutant SOD1 is reduced zinc binding[9], resulting in the transformation of the protein into a toxic pro-oxidant[10]. It is hypothesized that the root of the toxic gain-of-function is an alteration in the structure of SOD1, one of the most stable cytoplasmic proteins[11]. This may be either through exposure of novel sites of interaction in SOD1 or loss of structure in the metal binding loops, but this has not been demonstrated in vivo. The in vivo demonstration that SOD1 misfolding is linked to ALS pathogenesis is required to substantiate the SOD1-ALS hypotheses and yield insight into the mechanism of SOD1-ALS.

The inventors created an in vitro model system[12] to study the in vivo SOD-1 misfolding pathway. The inventors hypothesized that the seemingly disparate theories of aberrant pro-oxidant activity and misfolding in SOD1-ALS are in fact linked: SOD1's normal antioxidant role incurs an occupational hazard of being oxidized and this is further exacerbated by its long half-life in motor neurons[12]. The accumulation of such oxidative insults could promote misfolding and aggregation. SOD1 normally exists as an obligate homodimer, each subunit of which binds one copper and one zinc atom. The inventors have previously shown that mutant SOD1 is more prone to oxidation-induced misfolding than wild-type SOD1 in vitro, and that both form unnatural partially folded monomeric and soluble oligomeric intermediates prior to aggregation[13]. There is a need to better understand the underlying mechanism of this disease and to determine if SOD1-ALS pathogenesis results from protein misfolding.

SUMMARY OF THE INVENTION

The present invention provides a novel binding protein that specifically binds to misfolded or monomeric superoxide dismutase 1 (SOD1) and not the native homodimeric form of SOD1. The invention provides an antibody that binds to an epitope within the SOD1 dimer interface, which is normally buried within the native obligate homodimer. This SOD1-Exposed Dimer-Interface Antibody (SEDI antibody), recognizes SOD1 conformations where the native dimer is disrupted or misfolded, exposing the normally hidden hydrophobic dimer interface.

One aspect of the invention is a binding protein that binds to misfolded or monomeric SOD1, wherein the binding protein does not bind to native homodimeric SOD1.

An additional aspect of the invention is a method of detecting or monitoring amyotrophic lateral sclerosis in a subject having or suspected of having amyotrophic lateral sclerosis, comprising contacting a sample from the subject with any one of the binding proteins of the invention, wherein amyotrophic lateral sclerosis is indicated, if the binding protein binds to a misfolded or monomeric SOD1 in the sample.

A further aspect of the invention is a method of identifying substances for the treatment or prevention of amyotrophic lateral sclerosis comprising:

(a) contacting a sample from a subject treated with a substance with any one of the binding proteins of the invention, wherein binding is indicative of the presence of misfolded or monomeric SOD1 in the sample, (b) detecting the level of binding in the sample, and (c) comparing the level of binding in the sample to the level of binding in a control, wherein an altered level of binding in the sample compared to the control is indicative of a substance for the treatment or prevention of amyotrophic lateral sclerosis.

Another aspect of the invention includes kits comprising the binding proteins of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

Figure 1:
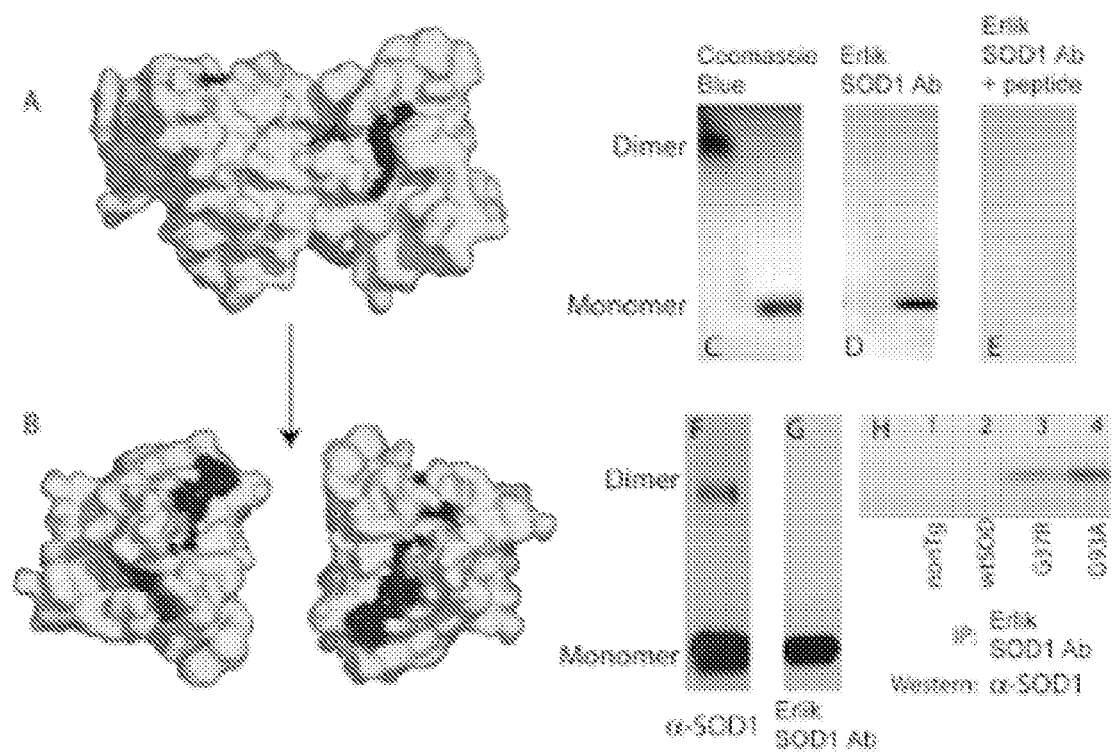
FIG. 1 shows the design and validation of SEDI antibody that selectively recognizes monomer/misfolded SOD1, but not native dimeric SOD1. A) Surface representation of native dimeric SOD1 with buried epitope shown in dark grey. B) Surface representation of monomeric SOD1 with now exposed epitope shown in dark grey. Figures were prepared using PyMol (Delano Scientific). C) SOD1, without heating under non-reducing conditions, runs primarily as a dimer in SDS-PAGE (lane 1, left), but runs predominantly as a monomer when boiled with reductant (lane 2, right). Stained with Coomassie Blue. D) SEDI antibody as the primary antibody in Western blot identical SOD1 SDS-PAGE gels as in C) detects only monomeric SOD1 and not dimeric SOD1. E) Specific SEDI antibody reactivity blocked by competition with excess antigenic peptide. F) Commercial SOD1 antibody (StressGen, Victoria), recognizes both monomeric and dimeric SOD1, whereas in G), SEDI antibody recognizes only monomeric SOD1 under identical conditions to F). H) Spinal cord homogenates from G37R and G93A SOD1 ALS-mouse models and non-transgenic littermate (of the G93A SOD1 mouse) and wild-type SOD1 overexpressing mouse were immunoprecipitated using the SEDI antibody. Misfolded SOD1 was found in the ALS-mouse models (lanes 3, 4), but not in the controls (lanes 1, 2).

DETAILED DESCRIPTION OF THE INVENTION (A) Binding Proteins

One aspect of the invention is a binding protein that binds to misfolded or monomeric (superoxide dismutase 1) SOD1, wherein the binding protein does not bind to native homodimeric SOD1.

"Superoxide dismutase 1" or "SOD1" is a protein that binds copper and zinc ions and is an isozyme responsible for destroying free superoxide radicals in the body. It is a soluble cytoplasmic protein and acts as a homodimer to convert naturally-occurring but harmful superoxide radicals to molecular oxygen and hydrogen peroxide.

The term "misfolded SOD1" as used herein refers to a non-native conformation of SOD1 that does not form a homodimer, which is thought to be its native conformation in vivo. The term "monomeric SOD1" as used herein refers to a single unit of SOD1. The unit may be non-native form of SOD1 that does not form a homodimer or the unit may be a single unit of a homodimer of native SOD1 that has been separated, for example under reducing conditions.

The term "binding protein" as used herein refers to proteins that specifically bind to another substance. In an embodiment of the invention, the binding proteins can bind to misfolded or monomeric SOD1, but does not bind to the native dimeric form of SOD1. In an embodiment of the invention, the binding proteins are antibodies or antibody fragments.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

Antibodies having specificity for a specific protein, such as misfolded or monomeric SOD1, may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the peptide and the monoclonal antibodies can be isolated.

The invention also contemplates the use of "peptide mimetics" for the binding proteins. Peptide mimetics are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of the binding proteins of the invention, such as its ability to bind to misfolded or monomeric SOD1. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to the binding proteins of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

In one embodiment of the invention, the binding protein binds to an epitope on the hydrophobic dimmer interface of SOD1, which it normally not exposed in its native homodimer form. For example, in one embodiment of the invention the epitope comprises the amino acid sequence ACGVIGI (SEQ ID NO:1). In another embodiment of the invention, the epitope comprises the amino acid sequence RLACGVIGI (SEQ ID NO:2). In a further embodiment of the invention, the epitope comprises the amino acid sequence GGRLACGVI-GIGGKG (SEQ ID NO:3).

The term "epitope" as used herein refers to the part of the misfolded or monomeric SOD1 which contacts the antigen binding site of the binding protein of the invention.

In a specific embodiment, the binding protein is an antibody that binds to the epitope ACGVIGI (SEQ ID NO:1), RLACGVIGI (SEQ ID NO:2), or GGRLACGVIGIGGKG (SEQ ID NO:3). In one embodiment the antibody is the SEDI antibody. As used herein, the SEDI antibody is alternatively referred to as the anti-SEDI antibody or the Erlik antibody or the Erlik SOD1 antibody.

(B) SOD1 Fragments

The invention also includes fragments of SOD1 comprising the epitopes ACGVIGI (SEQ ID NO:1), RLACGVIGI (SEQ ID NO:2), or GGRLACGVIGIGGKG (SEQ ID NO:3) or variants thereof.

The term "variant" as used herein includes modifications or chemical equivalents of the amino acid and nucleotide sequences of the present invention that perform substantially the same function as the proteins or nucleic acid molecules of the invention in substantially the same way. For example, variants of proteins of the invention include, without limitation, conservative amino acid substitutions. Variants of proteins of the invention also include additions and deletions to the proteins of the invention. In addition, variant peptides and variant nucleotide sequences include analogs and derivatives thereof.

A "conservative amino acid substitution", as used herein, is one in which one amino acid residue is replaced with another amino acid residue without abolishing the peptide's desired properties.

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The peptides constituting these epitopes can further comprise additional amino acid residues particularly at the N- and C-terminal flanks thereof, which may be useful in conjugating the epitope with an agent useful for instance in eliciting an immune response, or an agent serving as a tag useful in the production of the epitope or to monitor its presence. For instance, the epitope may further comprise an N-terminal Cys residue to assist with coupling to KLH or the like. The epitope may further comprise a linker effective to couple the epitope tandemly to another copy of the same or a different epitope. Alternatively, the epitope may further comprise a polyhistidine or Flag tag. In another embodiment, the epitopes may comprise additional amino acids that enhance the immunogenicity or solubility of the epitope. In one embodiment, the additional amino acids number from 1 to about 10, preferably 1 to 8, more preferably 1 to 5. Importantly the additional residues do not materially affect the conformation of the epitope.

In one embodiment, the variant amino acid sequences of the amyotrophic lateral sclerosis-specific epitopes have at least 60%, preferably at least 70%, more preferably at least 80%, and even more preferably at least 90% sequence identity to the above sequences. The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm[50], together with BLOSUM 62 scoring matrix[51] and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch[52], as revised by Smith and Waterman[53] so that the highest order match is obtained between the two sequences and the number of identical amino acids is determined between the two sequences. Other methods to calculate the percentage identity between two amino acid sequences are generally art recognized and include, for example, those described by Carillo and Lipton[54] and those described in Computational Molecular Biology[55]. Generally, computer programs will be employed for such calculations. Computer programs that may be used in this regard include, but are not limited to, GCG[56] BLASTP, BLASTN and FASTA[57].

The fragments of SOD1 of the present invention are useful as antigens in preparing antibodies that bind to misfolded or monomeric SOD1 but do not bind to the native dimeric form of SOD1. Antibodies to the SOD1 fragments can be prepared using techniques monomeric as described above in Section (A).

Accordingly, in one embodiment the invention provides a method of making an antibody that binds to misfolded or monomeric SOD1 comprising the following steps:

a) immunizing a host with an immunogen comprising an isolated SOD1 fragment wherein the isolated SOD1 fragment comprises the sequence ACGVIGI (SEQ ID NO:1), RLACGVIGI (SEQ ID NO:2), or GGRLACGVIGIGGKG (SEQ ID NO:3);
b) isolating an antibody from said host that binds misfolded or monomeric SOD1.

(C) Diagnostic Methods and Agents

The binding proteins of the invention selectively bind to misfolded or monomeric forms of SOD1 and not to the native dimeric form of SOD1. Misfolded or monomeric form of SOD1 present on or in a cell can be indicative of amyotrophic lateral sclerosis. Thus, the binding proteins of the invention can be used for the diagnosis, detection and monitoring of amyotrophic lateral sclerosis. Amyotrophic lateral sclerosis is a rapidly progressive, invariably fatal neurological disease that attacks the nerve cells (neurons) responsible for controlling voluntary muscles.

Accordingly, the invention includes methods of detecting or monitoring amyotrophic lateral sclerosis in a subject having or suspected of having amyotrophic lateral sclerosis, comprising contacting a sample from the subject with any one of the binding proteins of the invention, wherein amyotrophic lateral sclerosis is indicated, if the binding protein binds to a misfolded or monomeric SOD1 in the sample.

One aspect of the invention is a method of detecting or diagnosing amyotrophic lateral sclerosis in a subject comprising the steps of:

(a) contacting a test sample of said subject with an antibody of the invention, wherein the antibody binds to an amyotrophic lateral sclerosis-specific epitope to produce an antibody-antigen complex;

(b) measuring the amount of the antibody-antigen complex in the test sample; and (c) comparing the amount of antibody-antigen complex in the test sample to a control wherein a difference in the amount of antibody-antigen complex in the test sample as compared to the control is indicative of amyotrophic lateral sclerosis. The phrase "detecting or monitoring amyotrophic lateral sclerosis" refers to a method or process of determining if a subject has or does not have amyotrophic lateral sclerosis or the extent of the amyotrophic lateral sclerosis. In addition, the binding proteins of the invention can be used to detect or monitor the appearance and progression of the disease.

A control can be used in the method. The term "control" as used herein refers to a sample from an individual or a group of subjects who are either known as having amyotrophic lateral sclerosis or not having amyotrophic lateral sclerosis.

The term "subject" as used herein refers to any member of the animal kingdom, preferably a human being.

The term "sample" as used herein refers to any fluid, cell or tissue sample from a subject which can be assayed for misfolded or monomeric SOD1. In one embodiment, the sample comprises, without limitation, cerebrospinal fluid, plasma, blood serum, whole blood, spinal cord tissue, brain cells, motor neurons, a portion of the dorsal horn, or peripheral blood cells, such as erythrocytes, mononuclear cells, lymphocytes, monocytes and granulocytes.

In one embodiment of the invention, binding proteins, such as antibodies or antibody fragments, are used to determine if misfolded or monomeric SOD1 is present in the sample. In another embodiment, the binding proteins are labeled with a detectable marker. The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the detectable signal is detectable indirectly. For example, a secondary antibody that is specific for the binding protein of the invention and contains a detectable label can be used to detect the binding protein of the invention.

A person skilled in the art will appreciate that a number of methods can be used to determine if misfolded or monomeric SOD1 is present in a sample using the binding proteins of the invention, including immunoassays such as flow cytometry, Western blots, ELISA, and immunoprecipitation followed by SDS-PAGE immunocytochemistry.

In one embodiment of the invention, amyotrophic lateral sclerosis can be detected or monitored in a subject using flow cytometry of a sample from the subject, including peripheral blood cells, such as erythrocytes, mononuclear cells, lymphocytes, monocytes and/or granulocytes, or mononuclear cells found in cerebrospinal fluid. In a further embodiment, the cells assayed using flow cytometry can be permeabilized using reagents known to persons skilled in the art including, without limitation, detergents, ethanol, methanol and paraformaldehyde.

Any of the methods of the invention to diagnose, detect or monitor amyotrophic lateral sclerosis can be used in addition or in combination with traditional diagnostic techniques for amyotrophic lateral sclerosis. Traditional diagnostic techniques for amyotrophic lateral sclerosis include physical and neurological examinations, and can include electromyography tests, nerve condition velocity tests, and magnetic resonance imaging.

(D) Drug Screening

The binding proteins of the invention can also be used to identify and screen for substances useful for the treatment or prevention of amyotrophic lateral sclerosis or the formation of misfolded or monomeric SOD1, which is associated with amyotrophic lateral sclerosis. For example, the method of identifying substances for the treatment or prevention of amyotrophic lateral sclerosis can include:

(a) contacting a sample from a subject treated with a substance with any one of the binding proteins of the invention, wherein binding is indicative of the presence of misfolded or monomeric SOD1 in the sample, (b) detecting the level of binding in the sample, and (c) comparing the level of binding in the sample to the level of binding in a control, wherein an altered level of binding in the sample compared to the control is indicative of a substance for the treatment or prevention of amyotrophic lateral sclerosis.

A person skilled in the art will appreciate that the control can be a sample from a subject not treated with a substance or treated with a substance that is known not to treat or prevent amyotrophic lateral sclerosis. Thus, a reduced level of binding in the sample compared to the control is indicative of a substance for the treatment or prevention of amyotrophic lateral sclerosis. In addition, the control can be a sample from the same subject, but before treatment with the substance to be tested or samples from the subject taken at different points of time during treatment with the substance to be tested.

Substances for the treatment or prevention of amyotrophic lateral sclerosis can also be identified using cells or cell lines. For example, cells or cell lines can be contacted with a substance and then the presence of misfolded or monomeric SOD1 on the cells can be detected using the binding proteins of the invention and compared to a control.

A person skilled in the art will appreciate that a library of molecules can be screened by monitoring the effect of the candidate compounds on the inhibition of the conversion of SOD1 to a misfolded or disease-specific conformation.

The invention also includes the substances identified using the methods of the invention, which are useful for the treatment of amyotrophic lateral sclerosis or the formation of misfolded and/or aggregated SOD1, which is associated with amyotrophic lateral sclerosis.

(E) Kits

A further aspect of the invention is a kit for diagnosing, detecting or monitoring amyotrophic lateral sclerosis comprising any one of the binding proteins of the invention and instructions for use. In one embodiment of the invention, the binding is labeled using a detectable marker.

The following non-limiting examples are illustrative of the present invention:

Examples

Materials and Methods

Antibody Generation and Purification

Peptide synthesis was carried out using standard Fmoc-based chemistry on a Perseptives Biosystems 9050 Plus Pep-synthesizer. The multiple antigenic peptide was synthesized on a [Fmoc-Lys(Fmoc)]$_4$-Lys$_2$-Lys-Cys(Acm)-β-Ala-Wang resin (Advanced ChemTech, SM5104, Louisville, Ky.) using Fmoc-protected amino acids (Advanced ChemTech; Nova-biochem, San Diego, Calif.; Applied Biosystems, Foster City, Calif.). The sequence was Acetyl-GGRLACGVIGIGGKG-(SEQ ID NO:3); composition and sequence were verified by amino acid analysis and peptide synthesizer on-line UV-absorbance analysis. This peptide was cleaved and purified by dialysis versus 10 mM Tris, 10 mM sodium acetate (Sigma); dialysis was carried out at pH 8.0 to allow disulfide bond formation between adjacent strands of the peptide dendrimer. The MAP antigen had a molecular weight of ~11 kDa and was used without conjugation to a carrier protein. The antigen was sent to Sigma-Genosys (Oakville, Ontario, Canada) for rabbit antiserum production (manufacturer's 'partial package'). Antiserum production followed standard protocol (Sigma-Genosys) and was in accordance with the Animal Welfare Act (USA).

A linear peptide with identical sequence to the antigen was synthesized on a [non-cleavable] TentaGel-SH resin (Advanced ChemTech). This resin was deprotected and packed into disposable columns (Evergreen Scientific, Los Angeles, Calif.) for antiserum purification. Anti-serum was pre-cleared by centrifugation (16,000×g) and diluted 1:10 in tris-buffered saline (TBS) prior to purification. Dilute anti-serum was re-circulated over the affinity purification column 3× at a flow rate of ~1 ml/min at room temperature for binding. The antibody-bound column was washed with a minimum of 100 ml of TBS (~1 ml/min), until the wash eluent had no protein ($A_{280}$=0). Antibody fractions were eluted with 50 mM glycine, pH 2.8 into 1/5 volume ice-cold 1.5M Tris, 150 mM NaCl, pH 8.0, mixed and immediately placed on ice. These fractions were centrifuged 16,000×g and the concentration of the antibody in the supernatant was determined using an $\epsilon_{280}$=220,000 and an IgG molecular weight of 150,000 Da. Purification column was regenerated by excess washing with 50 mM glycine, pH 2.8, followed by treatment with saturated guanidine-HCl, 50 mM Tris, pH 8.0. Column was equilibrated with TBS prior to application of anti-serum. Only serum from the third bleed or later was used. In all cases, antibody was purified immediately prior to use and stored with 2 mg/ml BSA to stabilize the antibody.

SDS-PAGE and Western Blotting

SDS-PAGE was performed using the Tris-Glycine buffer system with pre-cast 4-20% poly-acrylamide gradient gels (Invitrogen, Carlsbad, Calif.). For partially denaturing gels (FIG. 1c-e), human erythrocyte SOD1 (Sigma) was either boiled for 15 minutes with 4% beta-mercaptoethanol (Aldrich) in SDS-loading buffer (denaturing, lane 2) or kept on ice for 15 minutes in SDS-loading buffer (partially denaturing, lane 1). 1-5 μg of SOD1 was run in each lane with equivalent results (5 μg shown in FIG. 1c-e). For Western blotting, gels were transferred onto PVDF membrane, blocked overnight in 5% milk-TBST (tris buffered saline, 0.05% Tween-20). 0.2 μg/ml (note: up to at least 5 μg/ml yielded equivalent results) SEDI SOD antibody diluted in 5% milk-TBST was used as the primary antibody, and 1:5000 dilution of anti-rabbit IgG-HRP (Stressgen, Victoria, Canada) was used as the secondary antibody. Western blots were developed using ECL-Plus (Amersham, Buckinghamshire, UK) and visualized on Kodak film. For peptide competition experiments (FIG. 1e, FIG. 4), diluted SEDI SOD antibody was pre-incubated with a 500× (molar) excess of free linear peptide with the same sequence as the antigen (synthesized as above) at 4° C. overnight or 1 hr. at room temperature prior to use.

In Vitro Immunoprecipitation Reactions

SOD1 from human erythrocytes (Sigma) was further purified when necessary by gel filtration chromatography. Stock 106 μM SOD1 in 50 mM Hepes, pH 7.5, was diluted to 2 μM final concentration in 8M urea, 2 mM dithiothreitol (DTT) and 1 mM ethylenediamine tetracetic acid (EDTA) overnight at room temperature. This is referred to as 'unfolded SOD1'. Unfolding of SOD1 was followed by tryptophan fluorescence on a Photon Technology International QM-1 fluorescence spectrophotometer; excitation wavelength: 280 nm and emission wavelength: 350 nm. This was diluted 1/20 phosphate buffered saline (PBS) to obtain refolding kinetics. Stock SOD1 was similarly diluted in PBS overnight ('folded SOD1'). 'Unfolded SOD1' or 'folded SOD1' were diluted 1/20 in PBS containing 5 μg/ml SEDI antibody and 2 mg/ml BSA (Sigma) as a stabilizer. This reaction was incubated for 1 hr at room temperature followed by immunoprecipitation with 50 μl of washed Protein A sepharose beads (Sigma), per reaction, for 1 hr at room temperature. Supernatants from each reaction were treated as a loading control. Samples were Western blotted, as above, except sheep anti-SOD1 (Oxis) was used to avoid cross-reactivity with the precipitating antibody. The anti-sheep IgG-HRP secondary antibody was from Chemicon.

Enzyme Linked Immunosorbent Assay (ELISA)

The ELISA plate was coated with 10 μg of antigen (SOD1 from human erythrocytes, Sigma; Lysozyme, Sigma) per well overnight at room temperature. After blocking with PBS+1% BSA w/v, aliquots (100 μl) of affinity (1 μg/ml) purified SEDI antibody or commercial (StressGen) antibody (1:20,000) were added to antigen coated microtiter plate and incubated at room temperature for 2 hours. After washing with PBS+ 0.05% Tween 20 v/v, 100 μl of HRP-conjugated anti-rabbit secondary antibody (1:5000) to wells and incubated at room temperature for 2 hours. After washing with PBS-Tween, 100 μl of TMB substrate was added to each well. Plates were read at 650 nm after 15 minutes incubation at room temperature.

Mutant SOD1 Transgenic Mice

Transgenic mice expressing the SOD1G93A mutation were purchased from The Jackson Laboratory (B6SJL-Tg (SOD1-G93A)1Gur/J; G1H high-expressor). The colony was maintained by breeding male heterozygous carriers to female B6SJLF1 hybrids. Transgenic mice expressing human WT SOD1 were used as control (B6SJL-Tg(SOD1)2Gur/J). Transgenic mice expressing SOD1G37R (line 29 G37R)[18] were maintained on a pure C57BL6 background. The lifespan of the G93A SOD1 transgenic mice was 120-140 days and for the G37R transgenic mice 11.5-12.5 months. G85R-SOD1 mice were from the original line 148, and have a lifespan of approximately 12 months[49].

All mice were genotyped by PCR. The use of animals as described was carried out according to *The Guide to the Care and Use of Experimental Animals of the Canadian Council on Animal Care*.

Immunoprecipitation Experiments

Mice were anesthetized in a $CO_2$ chamber prior to decapitation. Brain and spinal cords were immediately dissected and frozen on dry ice and weighed. Frozen tissue was cut into smaller pieces and homogenized (10% w/v) in 1× lysis buffer (100 mM NaCl, 10 mM EDTA, 10 mM Tris, 0.5% deoxycholate, 0.5% NP-40, pH 7.4) and 1× Roche EDTA-free Complete Protease Inhibitor (Roche) solution with a pellet-pestle homogenizer. This homogenate was centrifuged at 2000×g; the supernatant is referred to as the 'soluble fraction' and the pellet fraction is referred to as the 'insoluble fraction'. Tissue homogenates were immediately aliquoted and frozen at −80° C. prior to use. For experiments with the insoluble fraction, the pellet was resuspended in lysis buffer. Protein concentration was determined using the BCA protein assay (Pierce). 100 µg of protein, diluted to 1 ml with PBS containing 1× protease inhibitors was immunoprecipitated with 5-10 µg SEDI SOD coupled to Dynabeads M-280 Tosyl-activated magnetic beads (Dynal Biotech, Oslo, Norway) according to the manufacturer's instructions. Briefly, 100 µg of SEDI SOD IgG was dialyzed against 3 changes of PBS. This was incubated with 300 µl of pre-washed stock magnetic beads in PBS at 4° C. for a minimum of 96 hrs. This was followed by blocking with 0.1% BSA in 0.2M Tris, pH 8.5 for 24 hrs at 4° C. Equivalent results were obtained when using Protein G sepharose beads (Sigma) to precipitate SEDI SOD IgG in immunoprecipitation experiments.

Immunoprecipitation/Immunopurification Experiments

Samples were prepared as described for immunoprecipitation experiments described above. 750 µg of tissue homogenate in lysis buffer, diluted to 1 ml with PBS containing 1× protease inhibitors was immunoprecipitated (immunopurified) with 10 µg SEDI antibody coupled to Dynabeads M-280 Tosyl-activated magnetic beads (Dynal Biotech, Oslo, Norway). Equivalent results were obtained when using Protein G or Protein A sepharose beads (Sigma) to precipitate SEDI IgG in immunoprecipitation experiments. Immunoprecipitation reactions were washed 3× in PBS prior to boiling in reducing SDS sample buffer for Western blotting, as above.

Immunohistochemistry

Mice anesthetized with sodium pentobarbital were perfused transcardially with 10% methanol free phosphate buffered formalin (Fisher Scientific). Spinal cords were carefully dissected, paraffin-embedded and 6 µm sections cut either longitudinally or transversely using a rotary microtome. All sections for immunohistochemistry were treated with 3% $H_2O_2$ (v/v) and 10 mM sodium citrate buffer, pH 6.0 prior to labeling. The following antibodies were used: anti-SEDI SOD rabbit polyclonal (5 µg/ml); anti-TOM20 rabbit polyclonal (Santa Cruz Biotechnology, Calif.; 1:40); anti-human SOD1 sheep polyclonal (BioDesign; 1:500); anti-GFAP rabbit polyclonal (DakoCytomation; 1:200); and anti-Mac2 rat monoclonal antibody obtained from hybridomas (TIB-166) distributed by ATCC (Manassas, Va., 1:500). In all cases primary antibodies were left to react overnight at 4° C. Sections were developed using the DakoCytomation Envison™ System according to the manufacturer's instructions using 3,3'-diaminobenzidine (DAB) as chromagen. For double-labeling the DakoCytomation Envison™ DoubleStain kit was used with nitro-blue tetrazolium (NBT) as chromagen. Stained sections were visualized using a Leica DM 6000 microscope and digital images obtained with a Micropublisher 3.3 RTV digital color camera (Qimaging).

Subcellular Fractionation

Figure 13:
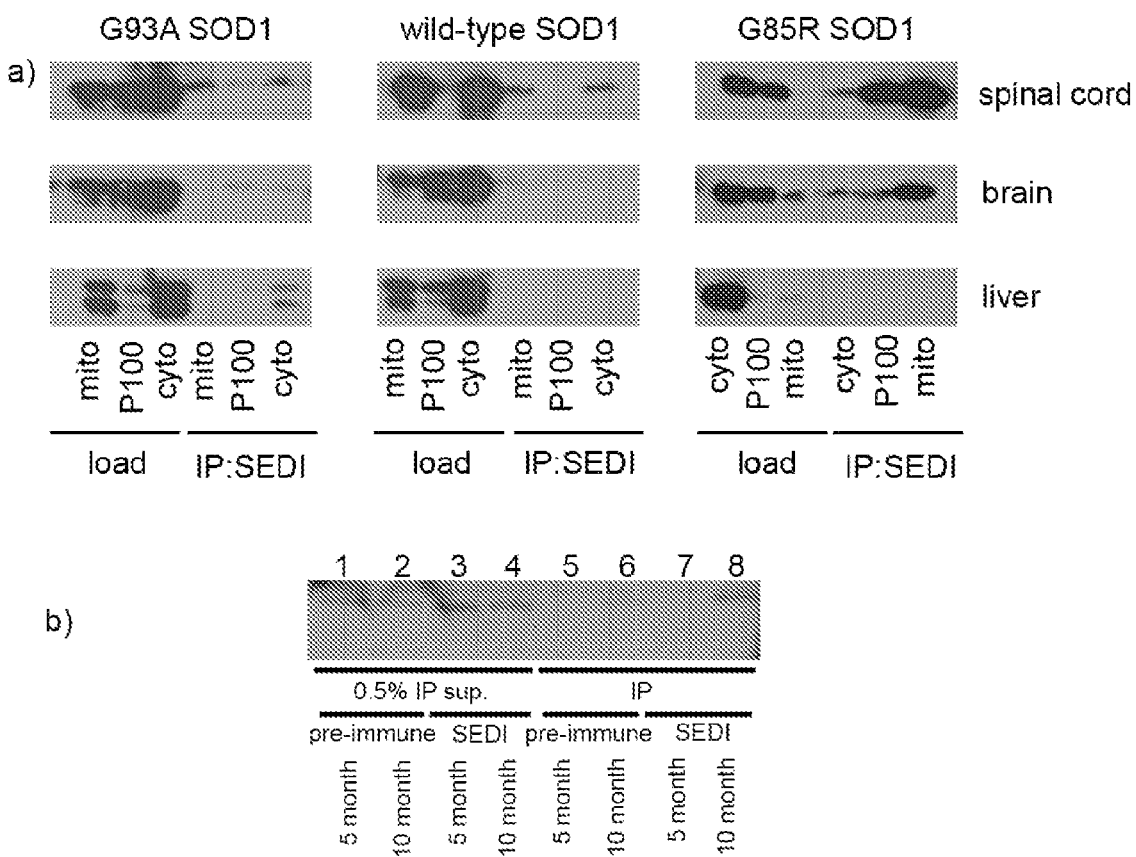
FIG. 13 shows the subcellular distribution of monomer/misfolded SOD1. a) Affected (spinal cord, brain) tissues and unaffected tissues (liver) were dissected from G93A SOD1 rats, wild-type SOD1 overexpressing rats or from G85R SOD1 mice. Tissues were fractionated as per Liu et al[5] and anti-SOD 1 Western blotting was performed as indicated in Materials and Methods. Loading controls ('load') were 0.25% of the immunoprecipitation reaction supernatant. 100 µg of protein from each sample was SEDI immunoprecipitated as indicated ('mito'=gradient purified mitochondria, 'P100'=100,000×g pellet, containing microsomes, 'cyto'=cytoplasm), except the G85R-SOD1 spinal cord mitochondrial fraction, 30 µg of which was used. b) Immunoprecipitation of solubilized mitochondrial fraction from G85R SOD1 spinal cords. The spinal cords from two 5 month old G85R SOD1 mice (and one non-transgenic littermate) were pooled and fractionated ('5 month'). Three 10 month old G85R SOD1 mice spinal cords were similarly pooled and fractionated ('10 month'). The mitochondrial fractions were solubilized in RIPA buffer and immunoprecipitated with SEDI and pre-immune IgG. The loading controls, 0.5% of the immunoprecipitation supernatant ('IP sup'), are shown in the first four lanes, followed by the immunoprecipitations ('IP'). SEDI immunoprecipitates monomer/misfolded SOD1 from the 10 month sample (lane 8), but not the 5 month sample (lane 7). Pre-immune IgG pulls out a trace amount of SOD1 from the 10 month sample (lane 6). The greater amount of SOD1 in the SEDI IP relative to the pre-immune IgG further demonstrates the specificity of this antibody for monomer/misfolded SOD1.

Spinal cord, brain and liver were harvested from age-matched (14.5 weeks), pre-symptomatic G93A-SOD1 (Taconic) and human wild-type SOD1 rats and pre-symptomatic 11 months G85R-SOD1 mice[49]. The spinal cords of three G85R-SOD1 littermates were pooled to produce an adequate mitochondrial fraction. Tissues were homogenized in a glass homogenizer containing 5 volumes homogenization buffer (HB; 210 mM mannitol, 70 mM sucrose, 10 mM Tris-HCl pH 7.5, 1 mM EDTA). Unbroken cells and debris were pelleted at 1000×g for 10 min. Pellets were washed twice with 0.5 volume HB. The combined supernatants were subsequently centrifuged at 17,000×g for 15 min to produce a crude mitochondrial pellet. The supernatant was recovered and centrifuged at 100,000×g for 1 hr yielding a cytosolic (supernatant) and membrane-containing P100 (pellet) fraction. The P100 fraction was further washed once in HB and finally resuspended in HB for analysis. The crude mitochondrial pellet was washed once with HB containing 50 mM KCl and subsequently loaded onto a discontinuous 20%-34% Nycodenz gradient and centrifuged at 52,000×g for 1.5 hr[35,45]. Mitochondria were collected at the 25%-30% interface and subsequently washed twice with HB, and finally resuspended in HB for analysis. Protein concentrations were determined using the BCA Protein Detection Kit (Pierce). For immunoprecipitation reactions, these fractions were solubilized in 100 µl solubilization buffer (100 mM NaCl, 10 mM EDTA, 10 mM Tris, 0.25% deoxycholate, 1% NP-40, pH 7.4) and 1× Roche EDTA-free Complete Protease Inhibitor (Roche) solution by repeated pipetting followed by incubation at 4° C. for 6 hrs. 100 µg of each sample was immunoprecipitated, except for experiments reported in FIG. 13, where 33 µg of 5 month old (from two mice, pooled) and 50 µg of 10 month old G85R SOD1 (from 3 mice, pooled) spinal cord mitochondria were used. The 5 month old G85R SOD1 mouse spinal cords were supplemented with an age-matched non-transgenic mouse spinal cord to produce a mitochondrial fraction with the same protein concentration as the 10 month old sample.

Results

Antibody Design and Validation

Investigating protein conformation in vivo is a challenging problem. One possible strategy is to design an antibody that will recognize specific misfolded conformations but not the native protein. This hypothesis-driven approach has been previously applied to other neurodegenerative disorders involving protein aggregation, but these designs have relied on low resolution biophysical information on the structure of the misfolded protein. The approach employs the use of detailed X-ray crystal structure data to design an antibody against misfolded SOD1[14, 15]. It was hypothesized that an antibody that recognizes an epitope inaccessible in native dimeric SOD1 but exposed in SOD1 aggregates and aggregation intermediates, would be capable of selectively detecting misfolded SOD1 in vivo. Examination of the X-ray structure of the native SOD1 dimer (pdb code: 1SPD)[16] shows that residues 145-151 (ACGVIGI) are sequestered in the SOD1 dimer interface and are inaccessible in native SOD1. An antibody raised against this epitope is hypothesized to recognize misfolded forms of SOD1 where the native dimer interface is disrupted and exposed, such as in monomers and non-native oligomers. Accordingly, the inventors have named this the SOD1-dimer interface antibody (SEDI antibody). The inventors synthesized a multiple antigenic peptide where each branch of the dendrimer had the sequence ggRLACGVIGIgkgkg; the capitalized sequence is part of the SOD1 sequence (residues 143-151; FIG. 1A-B). SOD1 residues 143 and 144 were added to the antigenic peptide to increase its solubility; the N-terminal and C-terminal Gly/Lys linkers were added to contextualize the epitope to an internal sequence, increase solubility, and increase molecular weight for enhanced immunogenicity. Rabbit anti-serum produced from immunization with this antigen was affinity purified using an immobilized linear peptide with identical sequence to the antigen. Western blots were performed to examine whether the antibody could discriminate between dimeric SOD1 and monomeric SOD1 with the selected epitope exposed. Native SOD1 is sufficiently stable that under non-reducing conditions SOD1 runs primarily as a dimer in SDS-PAGE (FIG. 1C, Lane 1). When reduced under denaturing conditions, it runs predominantly as the monomer, but with some dimer still detectable (FIG. 1C, Lane 2 and FIG. 1F). In these gels, the SEDI antibody reacts only with monomeric SOD1 and not with native dimeric SOD1 (FIG. 1D). This antibody will thus react with SOD1 conformers where the selected epitope is exposed, but not with native SOD1. This contrasts with commercially available SOD1 antibodies that detect both native and misfolded SOD1 indiscriminately (FIG. 1F-G). Competition with the antigenic peptide confirmed the specificity of the antibody (FIG. 1E). The SEDI antibody thus satisfies the design criteria and provides a unique tool for testing the in vivo hypotheses.

Monomer/Misfolded SOD1 in G85R, G93A and G37R-SOD1 ALS-Mouse Models

Immunoprecipitation experiments with the SEDI antibody were conducted on spinal cord tissue from G93A and G37R-SOD1 (enzymatically active mutants[42]) and G85R-SOD1 (enzymatically inactive mutant[42]) mouse models of SOD1-ALS to test for the presence of misfolded SOD1. These mice develop many of the pathological and clinical features of human ALS and are widely used models of the disease[17, 18]. Since the SEDI antibody was raised against a sequence identical in mouse and human SOD1, it recognizes endogenous mouse SOD1 as well as the transgenic human SOD1. Under non-denaturing conditions, antibody conjugated to magnetic beads detected misfolded SOD1 from the soluble fraction of spinal cord homogenates of G93A and G37R-SOD1 mice, but not from non-transgenic littermates of the G93A mouse (FIG. 1H).

Figure 14:
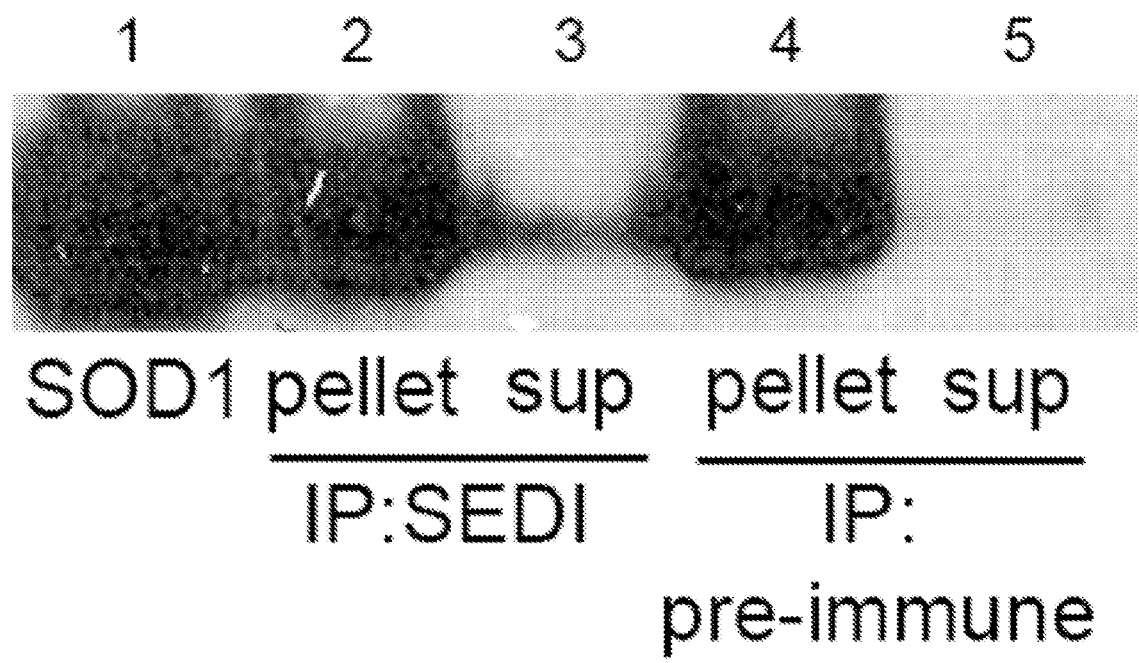
FIG. 14 illustrates that SEDI pulls out monomer/misfolded SOD1 from G93A-SOD1 spinal cord homogenates in immunoprecipitation reactions but the pre-immune IgG does not.
Figure 15:
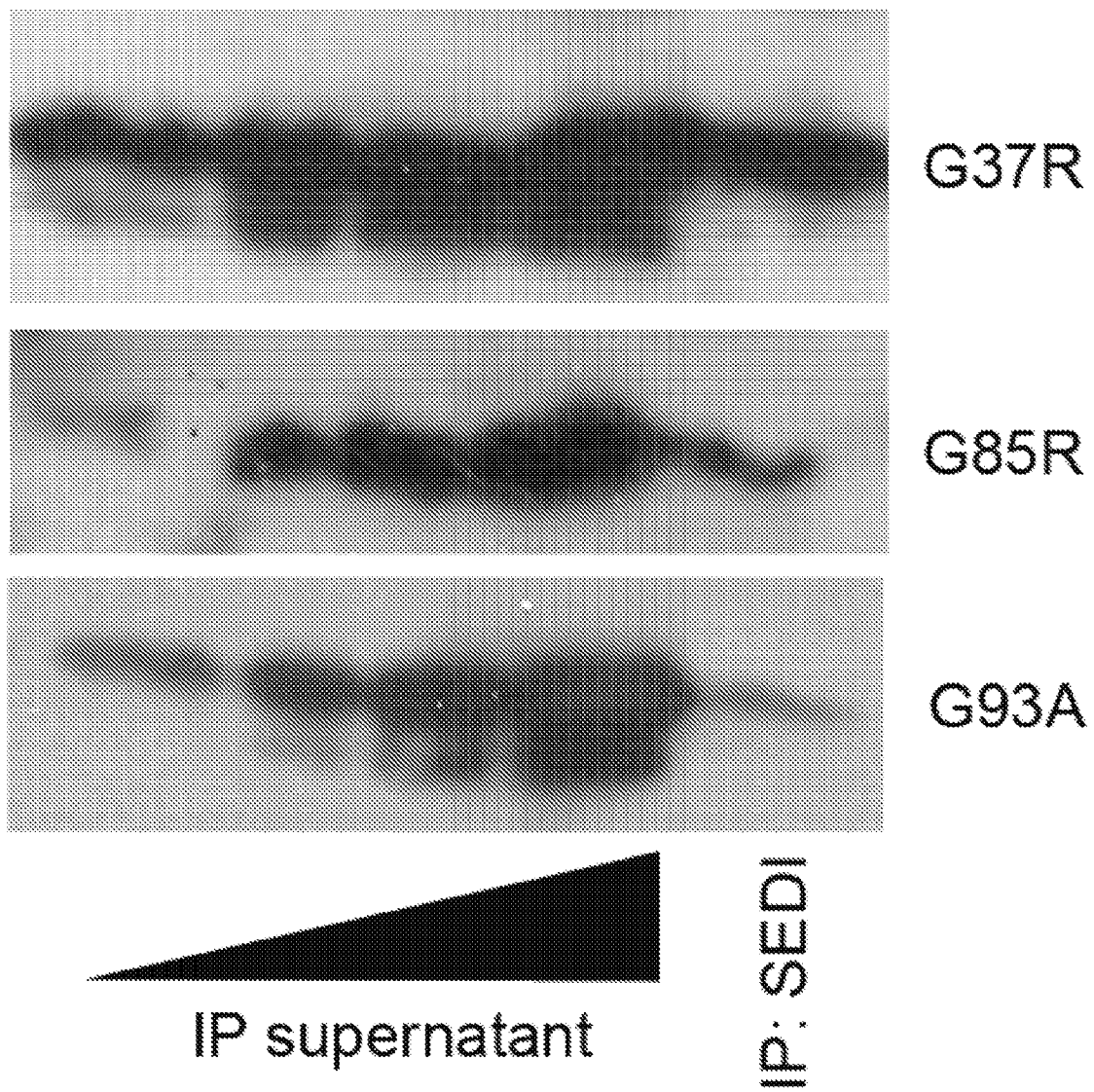
FIG. 15 shows that the total amount of monomer/misfolded SOD1 in the spinal cord homogenates of each of the three ALS-mice tested (G93A, G37R or G85R-SOD1 transgenic mice) is less than 0.5% of the total amount of SOD1. Anti-SOD1 Western blot alongside SEDI immunoprecipitations from 750 µg of G37R (top), G85R (middle) or G93A (bottom) SOD1 ALS-mouse spinal cord homogenates. Lanes 1-4 are 1 µl, 2 µl, 4 µl and 10 µl of 0.5% immunoprecipitation supernatant; the lower bands in the G37R and G93A spinal cord correspond to endogenous mouse SOD1. G85R SOD1 runs at the same molecular weight as mouse SOD1. Lane 5 is the SEDI immunoprecipitation with 10 µg of antibody.

Non-specific binding was minimal since only trace levels of SOD1 were precipitated with pre-immune IgG conjugated beads (FIG. 14, lane 5)[43]. In order to judge how much misfolded SOD1 is present in these mice, semi-quantitative Western blots were performed contemporaneously with the immunoprecipitation reactions (FIG. 15). At 80 days of age, 0.024% of G93A SOD1, 0.15% of G37R SOD1 at 8.5 months of age and 0.34% of total (mouse and human G85R) SOD1 from 11-month old G85R SOD1 ALS-mice are immunoprecipitated with SEDI in molar excess. The G127X-SOD1 ALS model expresses a natively unfolded truncated protein that accumulates to very low levels, but is sufficient to cause disease[44]. The accumulated levels of the truncated protein are comparable to the amounts of monomer/misfolded SOD1 in the models examined. This is the lower limit of total misfolded SOD1 since only soluble misfolded species are included and quantitative binding to SEDI is assumed. Only a subset of the mutant protein is misfolded in these mice.

Figure 2:
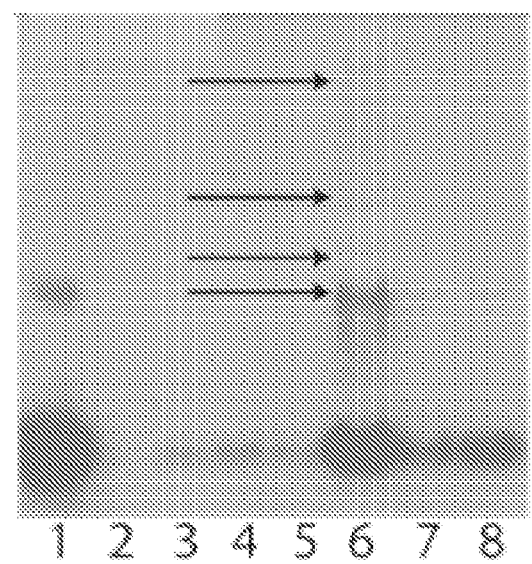
FIG. 2 shows the immunoprecipitation of misfolded SOD1 from wild-type SOD1 overexpressing mouse and detection of misfolded SOD1 in insoluble brain extracts from G93A mice. lanes: 1—SOD1 (no IP), 2—non-transgenic mouse spinal cord supernatant, 3—wtSOD1 brain pellet, 4—wtSOD1 brain supernatant, 5—wtSOD1 spinal cord supernatant, 6—G93A brain pellet, 7—G93A brain supernatant, 8—G93A spinal cord supernatant.

Small amounts of misfolded SOD1 were also occasionally immunoprecipitated from the spinal cords of mice overexpressing wild-type human SOD1 (FIG. 2, Lanes 3-5). To determine whether SEDI antibody reactive SOD1 is present in only the soluble fraction as monomers or soluble oligomers, or also as misfolded aggregates in the insoluble fraction, the pellet fractions of brain homogenates of G93A and wild-type SOD1 overexpressing mice were resuspended and immunoprecipitated. Misfolded SOD1, including SDS-resistant higher molecular weight oligomers, was found in the G93A pellet fractions (FIG. 2). This demonstrates that insoluble misfolded aggregates as well as soluble misfolded monomeric/oligomeric SOD1 are present in SOD1-ALS and are detectable by the SEDI antibody.

Motor Neuron Selective Deposition of Monomer/Misfolded SOD1

Figure 3:
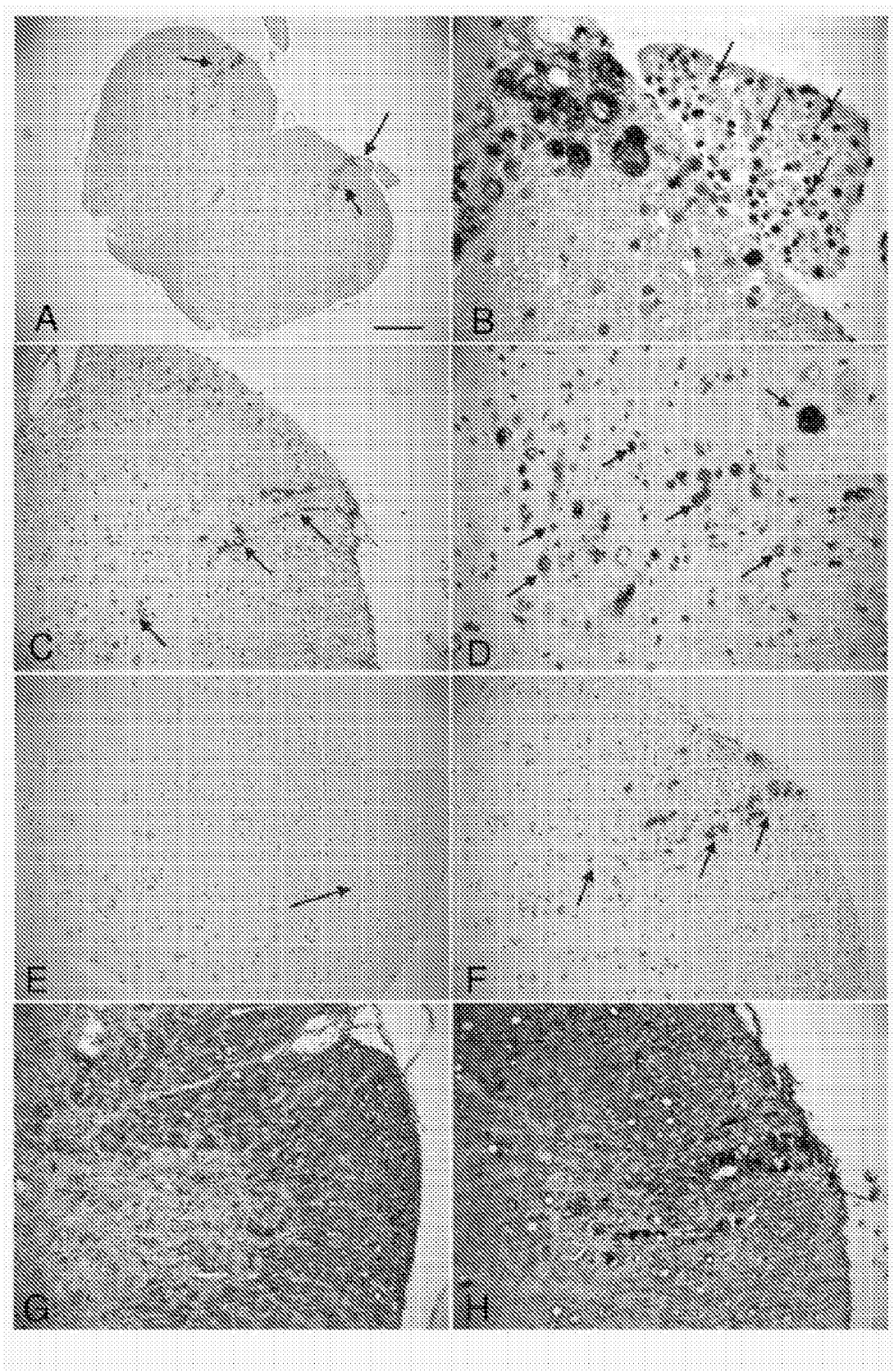
FIG. 3 shows that misfolded SOD1 deposits predominantly on the periphery of vacuoles in motor neurons in ALS-mice A) Cross section of G37R SOD1 mouse spinal cord; misfolded SOD1 (labeled with SEDI antibody, marked with arrows) is most abundant in the ventral horn. All sections counter-stained with hematoxylin. B) Misfolded SOD1 present in vacuoles in the axons of motor neurons (ventral root, G37R SOD1 mouse) (arrows). C) SEDI antibody staining (arrows) of G93A-SOD1 mouse spinal cord ventral horn follows neuritic tracts. D) Cross section of G93A SOD1 mouse spinal cord; misfolded SOD1 is found predominantly on the periphery of vacuoles (arrows). D) (inset) Inclusion bodies, similar to those reported earlier[19], also contain misfolded SOD1, but constitute a minor fraction of total misfolded SOD1. E) SEDI antibody staining of spinal cord ventral horn from non-transgenic mouse littermate of the G93A-SOD1 mouse, note: absence of staining. F) SEDI antibody staining of spinal cord ventral horn from transgenic mouse overexpressing human wild-type SOD1, note: limited staining of ventral horn. G) and H) SOD1 is ubiquitous and found in every cell type; labeled with non-discriminating commercial SOD1 antibody (Biodesign; G) G93A-SOD1 mouse, H) G37R-SOD1 mouse). Scale bar: A) 400 µm.

Localization of misfolded SOD1 in the spinal cords of G93A and G37R-SOD1 transgenic animals was examined using immunohistochemistry. The labeling with the SEDI antibody was strikingly specific, labeling vacuolated structures within motor neurons of the ventral horn and following the path of the ventral root in both G37R-SOD1 (8.5 months old) and G93A-SOD1 (100 days old) mice (FIGS. 3A, 3C).

Figure 4:
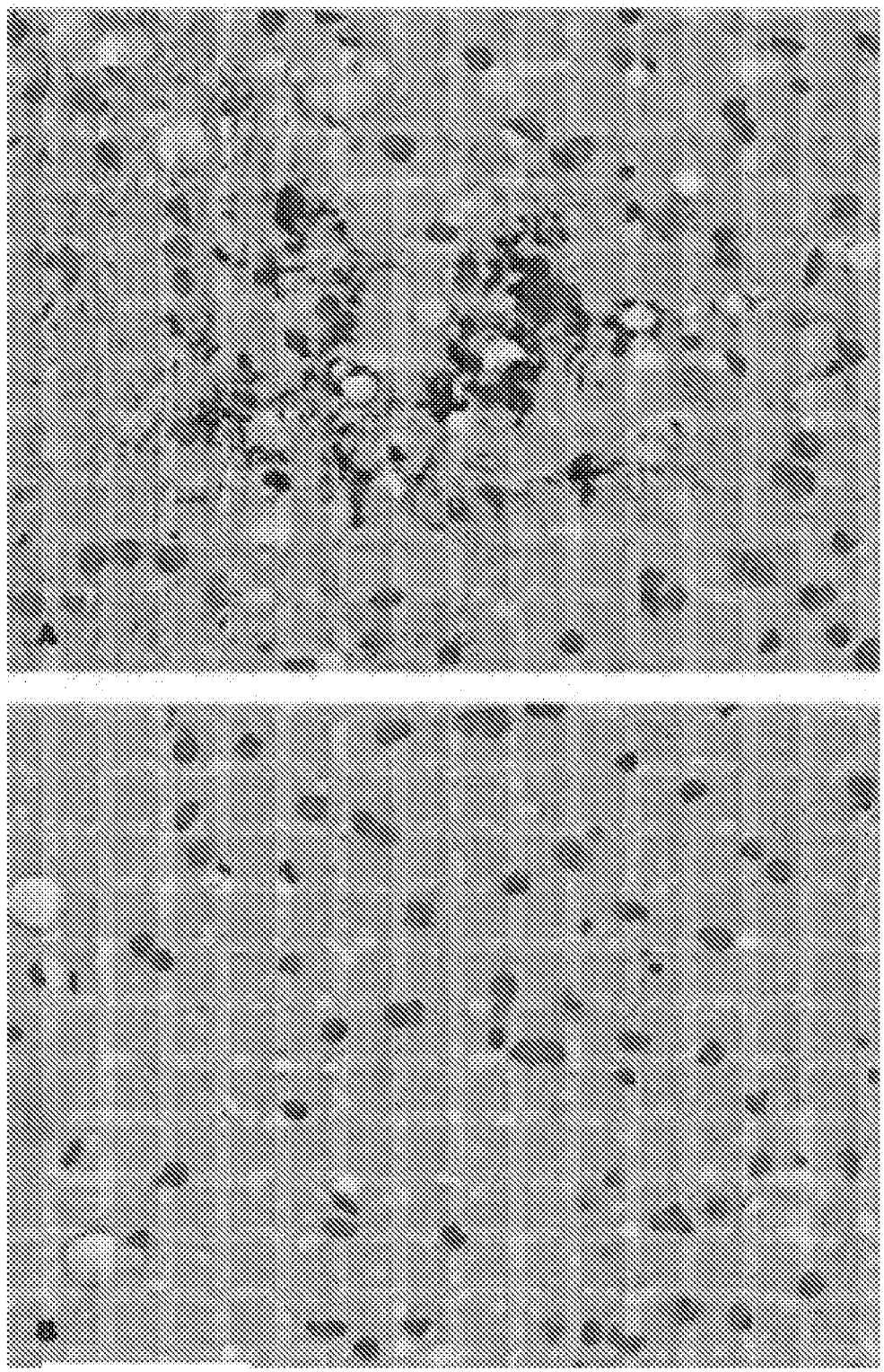
FIG. 4 shows that SEDI antibody labeling is specific and can be saturated by competition with the antigenic peptide. A) G93A mouse spinal cord labeled with SEDI antibody. B) Same as A), but antibody reaction competed with excess antigenic peptide.
Figure 5:
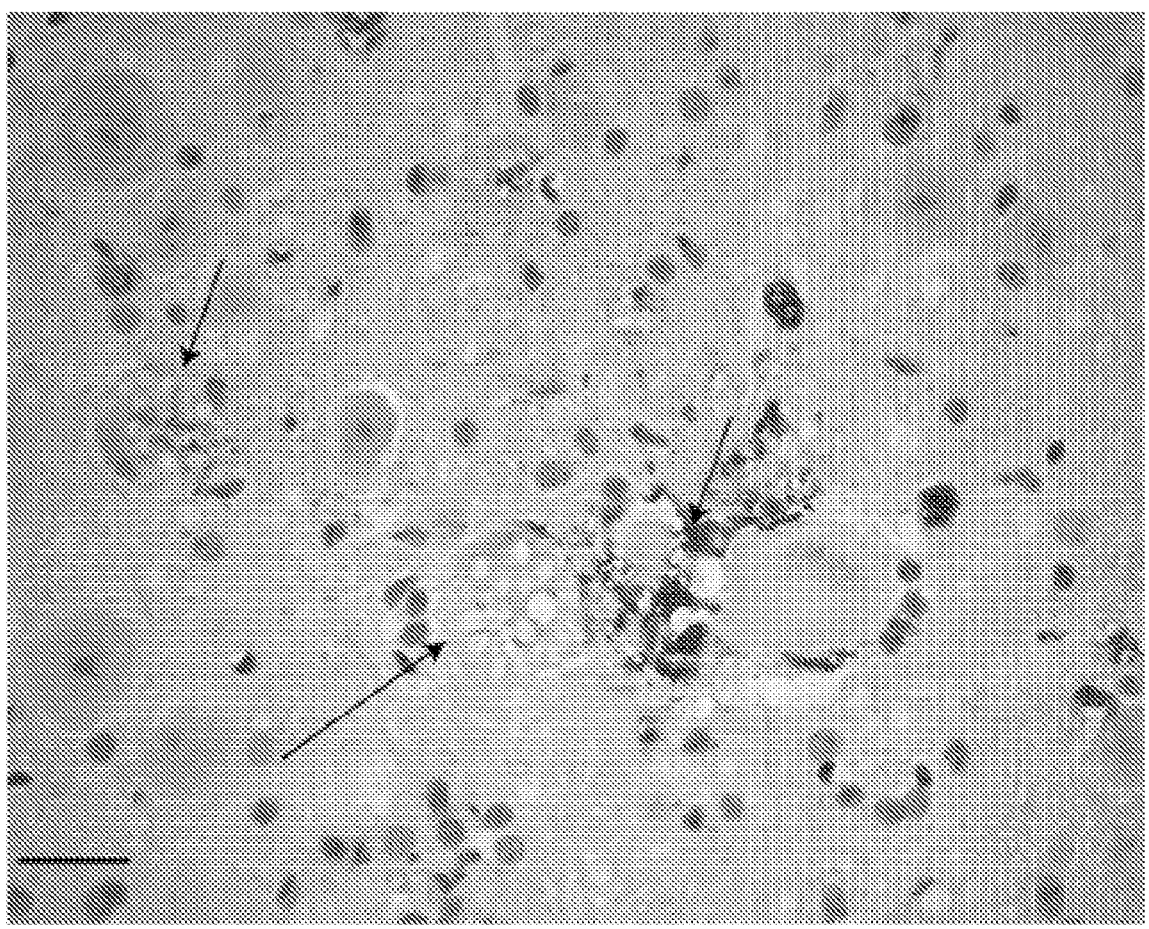
FIG. 5 shows that the major site of SEDI antibody staining is around vacuoles in ventral horn of G93A mouse spinal cord. Arrows: motor neurons containing large numbers of vacuoles with abundant SEDI antibody staining. Scale bar=25 µm.
Figure 6:
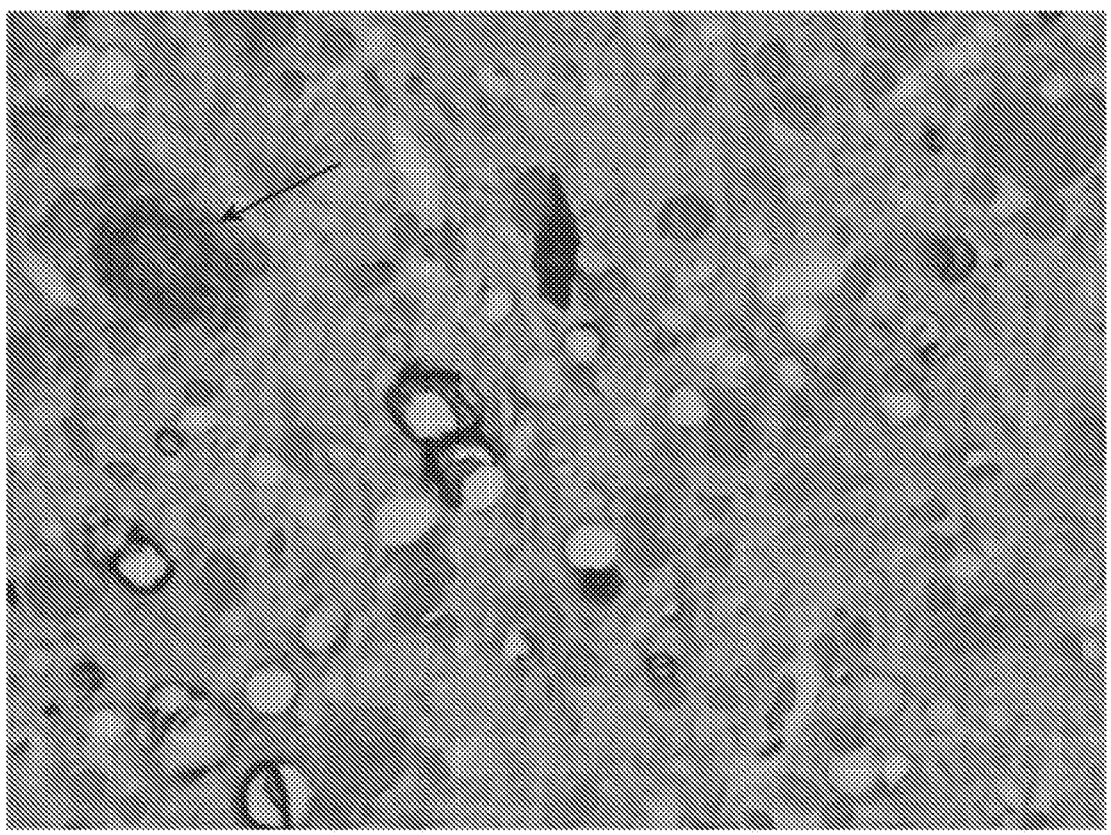
FIG. 6 shows that while the dominant structures labeled with SEDI antibody are vacuoles (FIGS. 3d, 5), labeling can also appear as diffuse staining of motor neuron perikaryon (arrow).
Figure 16:
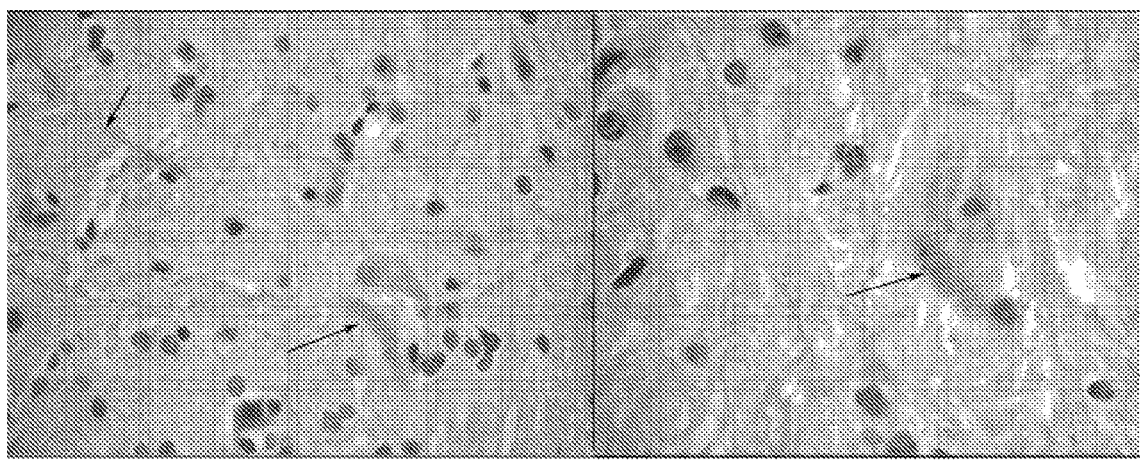
FIG. 16 shows immunohistochemical analysis of the G85R-SOD1 transgenic mouse spinal cord with the SEDI antibody. SEDI labels axonal processes in addition to inclusion bodies.

At higher magnification, the localization of misfolded SOD1 specifically to motor axons is clearly evident (FIG. 3B) as well as in axonal processes of the G85R-SOD1 mouse (FIG. 16). Furthermore, inclusion bodies in cells that morphologically appear to be motor neurons or astrocytes are detected with the SEDI antibody in G85R- (FIG. 16) and G93A-SOD1 spinal cord (FIGS. 3A, D). No labeling was observed in the dorsal horn or in axonal processes of the dorsal root (FIG. 3A), nor in spinal cord sections of non-transgenic littermates (FIG. 3E). It should be reiterated that SOD1 is a ubiquitous protein expressed in all cell types of the spinal cord. This is confirmed by the global distribution of SOD1 staining using the commercial antibody that recognizes both folded and misfolded SOD1 (FIG. 1F and FIGS. 3G, 3H). This is in contrast to the remarkable specificity of SEDI antibody labeling, which detects misfolded SOD1 predominantly in motor neurons (FIGS. 3A, 3C), and highlights the fact that although SOD1 is abundant in SOD1-ALS spinal cord, only a small fraction becomes misfolded or exists in the monomer/misfolded form. No staining is observed in the non-transgenic littermate of the G93A mouse, or when the specific antibody-antigen reaction is competed with the antigenic peptide (FIG. 4). Most of the monomer/misfolded SOD1 detected with the SEDI antibody is concentrated along the periphery of intracellular vacuoles in the spinal cords of G37R-SOD1 (FIG. 3A) and G93A-SOD1 (FIGS. 3D, 5) transgenic mice. Misfolded SOD1 can also appear as diffuse deposits within motor neuron perikarya (FIG. 6) illustrating that the SEDI antibody can detect low concentrations of misfolded SOD1, which is distinct from inclusion bodies and vacuolar deposits. SEDI antibody labeling also detects SOD1 within inclusion bodies (FIG. 3D, inset). However, this represents only a minor fraction of total antibody labeling within the mouse spinal cord. SOD1-inclusion bodies have been previously postulated as the toxic species in ALS[19], but the abundant labeling of perivacuolar and diffuse deposits throughout the spinal cord ventral horn suggests that these misfolded species may also play a significant role.

Wild-Type SOD1 can Misfold In Vivo

It has been suggested from in vitro studies that a pool of monomeric immature SOD1 exists in cells[20]; the absence of staining in the non-transgenic mouse (FIG. 3E) suggests that either monomeric immature SOD1 is present at levels below the detection limit of this antibody or that this antibody does not recognize immature SOD1. Interestingly, small amounts of misfolded SOD1 were also observed in atypical vacuoles in the mouse expressing high levels of human wild-type SOD1 (FIG. 3F). This is corroborated by the inventors' observation that small amounts of SOD1 are occasionally immunoprecipitated using the SEDI antibody from this mouse (FIG. 2) and that wild-type SOD1 can misfold in vitro[13]. It has been reported that transgenic mice overexpressing wild-type human SOD1 do develop pathological features of ALS but at much later stages than mice expressing the mutant protein and our finding of misfolded SOD1 localized to vacuoles in the wild-type SOD1 mouse is consistent with these previous findings[21]. Indeed, the presence of some misfolded SOD1 in the wild-type SOD1 mouse may explain a long-standing mystery: expression of mouse or human wild-type SOD1 is not neuroprotective[19], and high-level overexpression of human wild-type SOD1 can actually exacerbate disease by causing earlier onset in mice[21].

Vacuolated Mitochondria are the Primary Deposition Sites of Monomer/Misfolded SOD1

Figure 7:
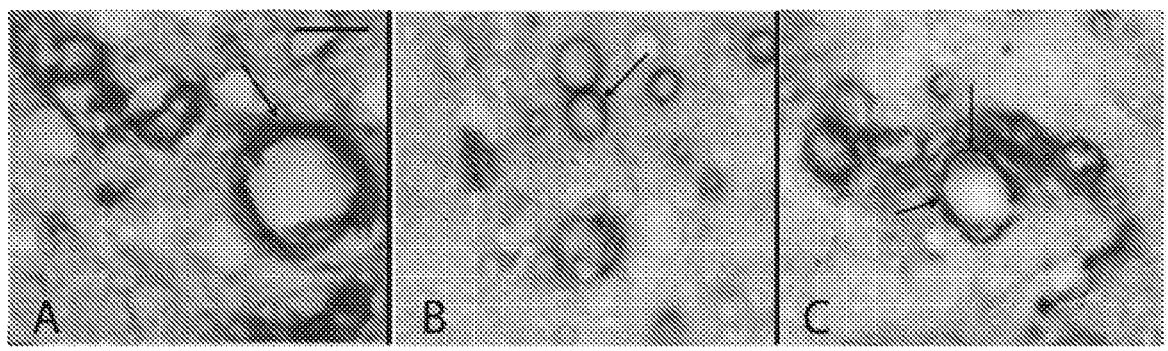
FIG. 7 shows that misfolded SOD1 localizes primarily to vacuolated mitochondria A) Misfolded SOD1 primarily localizes around vacuoles (arrow); counterstained with hematoxylin. B) Vacuoles labeled with marker for mitochondrial outer membrane, TOM-20 (arrow). Note: not counterstained with hematoxylin. C) Co-localization of misfolded SOD1 and TOM-20 (arrows). Scale bar (A)=10 µm.

Vacuolar degeneration of mitochondria is common in the pathology of G93A and G37R-SOD1 expressing mice[1] and SOD1 deposition on the surface of mitochondria undergoing vacuolarization by intermembrane space expansion has previously been reported[22]. To determine if the vacuoles, the major site of monomer/misfolded SOD1 deposition as seen with the SEDI antibody (FIGS. 3B, D), are dilated mitochondria, immunohistochemical double staining was conducted against the mitochondrial outer membrane protein, TOM20 and misfolded SOD1. Co-localization of the anti-TOM20 antibody and our antibody in motor neurons of the ventral horn indicates that the majority of misfolded SOD1 deposits around vacuolated mitochondria (FIG. 7A-C). This contrasts with the distribution of native dimeric SOD1, which is primarily cytosolic. Since mitochondria are the principle source of oxidative stress in vivo, the observation that misfolded SOD1 deposits primarily around vacuolated mitochondria is consistent with the hypothesis that oxidative stress triggers SOD1 misfolding[12]. The inventors note that vacuoles with peripheral membrane deposits of monomer/misfolded SOD1 are also present within axons of the ventral root (FIG. 3B).

Subcellular Localization of Monomer/Misfolded SOD1

The subcellular distribution of SEDI-reactive SOD1 was shown using immunoprecipitations from tissue fractions that had been prepared by differential and gradient centrifugation and immunohistochemical double labeling. SOD1 is classically defined as a cytoplasmic protein and is mitochondrially localized in certain instances. Disease affected (spinal cord, brain) and non-affected (liver) tissues from G93A- or (human) wild-type SOD1 overexpressing rats or G85R-SOD1 mice were homogenized and fractionated[45]. These fractions were solubilized in mild detergent and the protein concentration of each fraction was normalized prior to immunoprecipitations. In animals overexpressing enzymatically active protein, such as in the G93A-SOD1 and wild-type SOD1 overexpressing rats, misfolded SOD1 is present in both the mitochondrial and cytoplasmic spinal cord fractions, with only very small amounts detectable in the microsomal pellet fraction (P100) (FIG. 13A). In contrast, only minor amounts were immunoprecipitated from similar fractions isolated from liver and brain tissues collected from the same G93A SOD1 rat. In the case of the wild-type SOD1 overexpressing rat, misfolded SOD1 was nearly undetectable in all fractions obtained from brain and liver. Conversely, monomer/misfolded SOD1 was enriched by several magnitudes in spinal cord and brain mitochondria of G85R-SOD1 mice compared to the amount of monomer/misfolded species recovered from the cytosol. While the G85R-SOD1 mice express the protein to 10-50 fold lower levels than the G37R- and G93A-SOD1 mice, it has dramatically more monomer/misfolded SOD1 in the mitochondrial and membrane associated fractions of the spinal cord and brain. Immunoprecipitation reactions were also performed on the G85R SOD1 spinal cord mitochondrial fraction with pre-immune IgG; substantial amounts were pulled out with SEDI, but only a trace amount was pulled out with pre-immune IgG, showing that the SEDI surpasses any non-specific binding effect (FIG. 13B). A significant amount of monomer/misfolded SOD1 is detected in this fraction isolated from G93A- and G85R-SOD1 spinal cords. Native dimeric SOD1 is primarily cytosolic, as expected and no monomer/misfolded SOD1 was detected in any fraction of liver tissue. Since mitochondria are the principal source of oxidative stress in vivo, the observation that monomer/misfolded SOD1 deposits are concentrated on mitochondria, especially relative to the distribution of total SOD1, is consistent with oxidative stress triggering SOD1 misfolding[12].

A feature of the immunoprecipitation reactions of subcellular fractions with SEDI is that monomer/misfolded SOD1 displays a high affinity for membranous environments. The SEDI antibody recognizes a large stretch of hydrophobic residues normally buried in the native dimer interface. Consequently the binding of monomer/misfolded SOD1 to hydrophobic membrane environments may be mediated by the exposed hydrophobic dimer interface. Mutant SOD1 has increased hydrophobicity as shown by immunohistochemistry experiments showing concentration of monomer/misfolded SOD1 around vacuoles (FIG. 7A). These vacuoles are histopathological features observed in the G93A- and G37R-SOD1 mice, but not other mutant SOD1 mice[1]. These vacuoles have mitochondrial[18] and peroxisomal origins[22]; in fact, the colocalization of mitochondrial markers, such as Tom20, with SEDI labeling around these vacuoles is also observed (FIG. 7A-C). While mitochondrial association of G93A or G37R-SOD1 is implicated in vacuolization[22], the significant enrichment of monomer/misfolded SOD1 in the mitochondria of G85R-SOD1 mice (FIG. 13A), which do not possess vacuoles, shows that association of monomer/misfolded forms of SOD1 to mitochondria is not sufficient to cause vacuolization.

Figure 8:
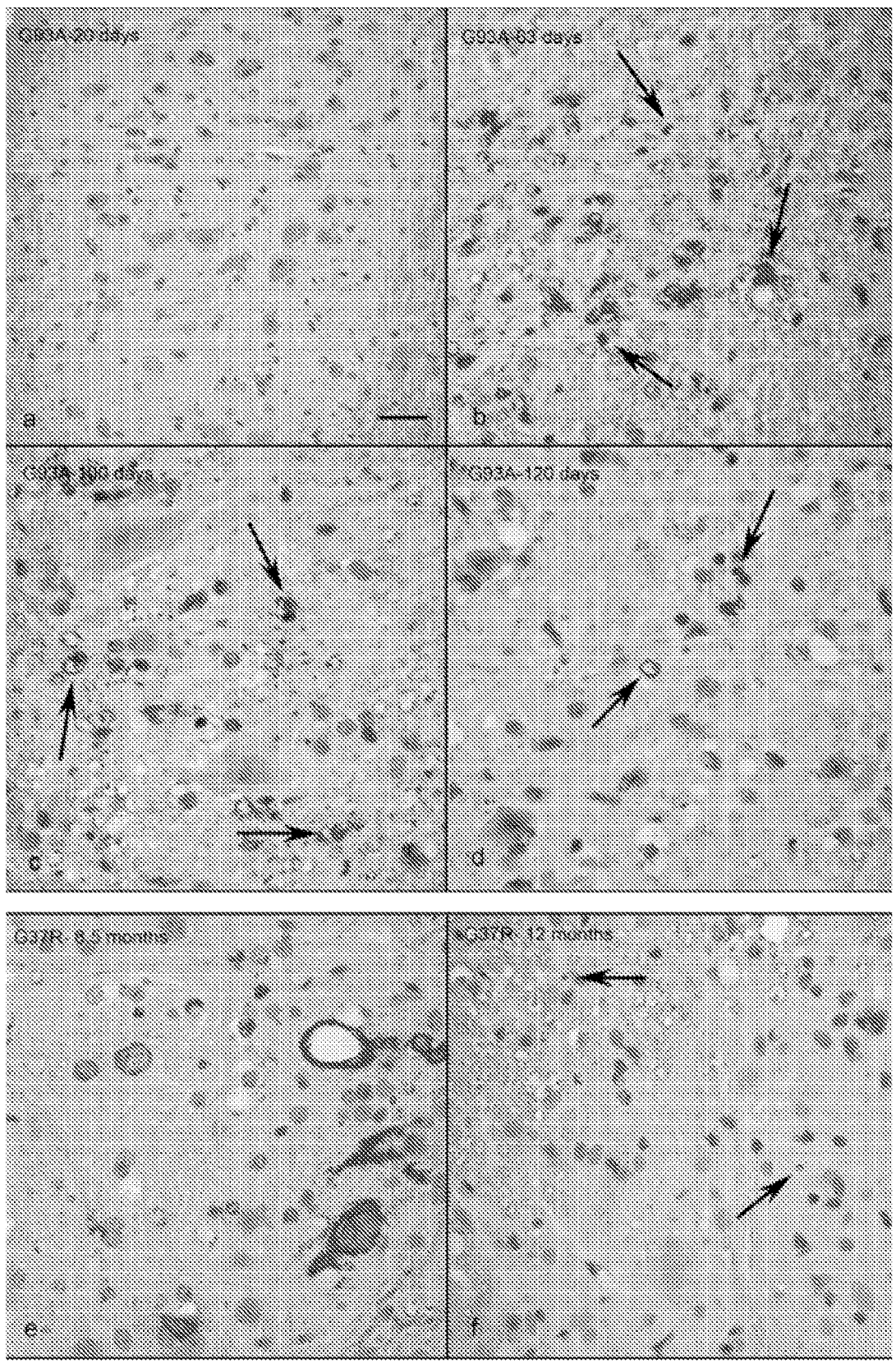
FIG. 8 shows age-dependent accumulation and decrease of misfolded SOD1 with concomitant loss of motor neurons in G93A-SOD1 model of ALS. A) Misfolded SOD1 is initially absent (age: 20 days). B) Misfolded SOD1 appears in pre-symptomatic G93A-SOD1 mouse spinal cord (arrows) (63 days). C) Misfolded SOD1 staining peaks at onset of rear-leg weakness (arrows) (100 days). D) Decline in levels of misfolded SOD1 at end-stage. Some misfolded SOD1 is still present as round deposits (arrows), but obvious vacuolar deposition is minimal (120 days). E) Misfolded SOD1 in G37R-SOD1 model of ALS at 8.5 months of age (pre-symptomatic) and F) 12 months of age (disease end-stage). Scale bar in A) 70 µm. SEDI antibody staining is in brown, hematoxylin counterstain is in blue.

Monomer/Misfolded SOD1 Appears Prior to Symptom Onset and Correlates with Motor Neuron Loss It is of both clinical and scientific importance to understand whether the burden of misfolded SOD1 may change with disease progression and age. Knowledge of the generation and accumulation of misfolded SOD1 is critical to the timing of potential therapeutics and may yield clues about the source of SOD1 denaturational stress. The inventors take advantage of the high degree of synchronicity in disease phenotype of the G93A-SOD1 mouse to monitor the appearance of misfolded SOD1 with age. In the colonies, these mice all develop progressive rear-leg weakness around 100 days of age and are no longer viable at 120-130 days of age. Disease onset is preceded by motor neuron loss[23] and mitochondrial vacuolization[21]. Mice at 20, 63, 100 and 120 days of age were examined for the presence of misfolded SOD1. Misfolded SOD1 was initially absent (20 days; FIG. 8a), but could be detected in presymptomatic mice by 63 days of age (FIG. 8b). Greater amounts of misfolded SOD1 were present at the onset of symptoms (100 days; FIG. 8c), but declined with a concomitant loss of motor neurons to levels less than those seen at 63 days at end stage (120 days; FIG. 8d). There are also reduced levels of labeling with the SEDI antibody at end stage in the G37R-SOD1 mouse, where the majority of motor neurons have degenerated (FIGS. 8e and f). These observations demonstrate a temporal linkage of SOD1 misfolding and motor neuron degeneration in these mice: monomer/misfolded SOD1 appears prior to motor neuron degeneration and disappears concomitant with motor neuron loss.

Monomer/Misfolded SOD1 in a Human Case of A4V SOD1-ALS

Figure 9:
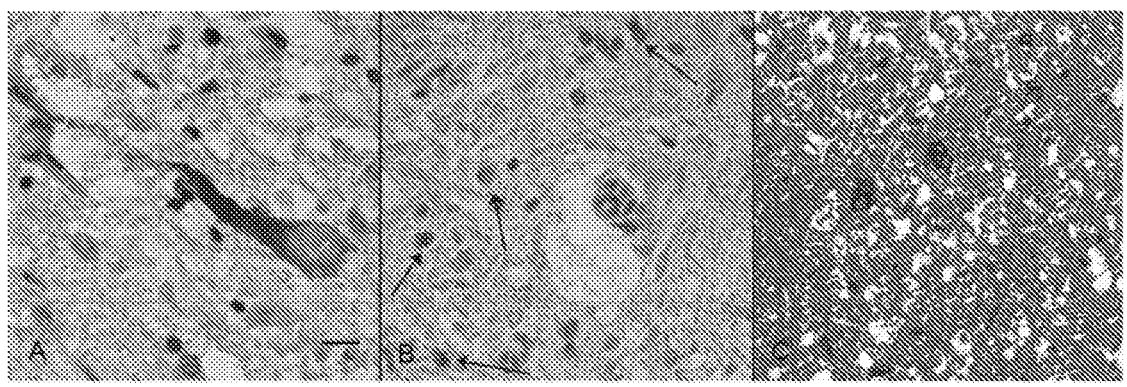
FIG. 9 shows misfolded SOD1 in a case of human SOD1-ALS. A) A motor neuron labeled with SEDI antibody in ventral horn of human spinal cord from ALS case carrying the A4V-SOD1 mutation. B) Misfolded SOD1 present as small round deposits in human A4V-SOD1 ALS parallels the round deposits observed in end-stage ALS-mouse models (FIGS. 8d, f). SEDI antibody staining is in brown, and hematoxylin counterstain is in blue. Scale bar=10 µm (A).

Spinal cord sections obtained at autopsy from a SOD1-ALS patient carrying the A4V SOD1 mutation were also examined with the SEDI antibody to test for the presence of monomer/misfolded SOD1. SEDI antibody labeling in the human case paralleled the observations of labeling in the end-stage ALS-mouse spinal cords. Both human and mouse spinal cords had reduced SEDI antibody staining and very few healthy motor neurons at disease end-stage; however, clear motor neuron labeling was seen in the human spinal cord with the SEDI antibody (FIG. 9A). We also found numerous small deposits of misfolded SOD1 (FIG. 9b) that are morphologically similar to those found at the disease end stage in mouse models of ALS (FIGS. 8D, 8F). This confirms the presence of misfolded SOD1 detected with the SEDI antibody in a human case of ALS.

Discussion

Based on in vitro biochemical data showing that SOD1, normally a stable obligate homodimer, forms a partially folded monomer aggregation intermediate[13], an antibody that selectively recognizes misfolded forms of SOD1 where the native dimer interface is exposed was designed. The SEDI antibody, a direct in vivo probe of SOD1 conformation, has established the presence of monomer/misfolded SOD1 in a human A4V SOD1-ALS case, a rat model of ALS and three different mouse models of ALS (G85R, G93A and G37R-SOD1); thus, at least four different SOD1 mutations form monomer/misfolded SOD1 in vivo. This was true for mice with highly expressed, enzymatically active G93A- and G37R-SOD1 as well as lower expressed, enzymatically inactive and physiologically unstable G85R-SOD1. SOD1-ALS can now be properly described as protein misfolding disease. This antibody was used to show that monomer/misfolded SOD1 is primarily localized to motor neurons, the locus of ALS pathology, whereas native states of both wild-type and mutant SOD1 is ubiquitous and found in all cell types. It is shown, for the first time, that the majority of these misfolded forms of SOD1 is concentrated around vacuolated mitochondria rather than in inclusion bodies. Since misfolded SOD1 monomers or oligomers are deposited on dystrophic mitochondria, this implicates a role for these species in SOD1-ALS toxicity.

Oligomeric misfolded species are also implicated in other protein misfolding disorders. It was recently discovered that soluble oligomers of alpha-synuclein in Parkinson's disease[24] and Aβ in Alzheimer's disease[25, 26] are highly neurotoxic species that contribute to neurodegeneration in these protein misfolding diseases.

Figure 10:
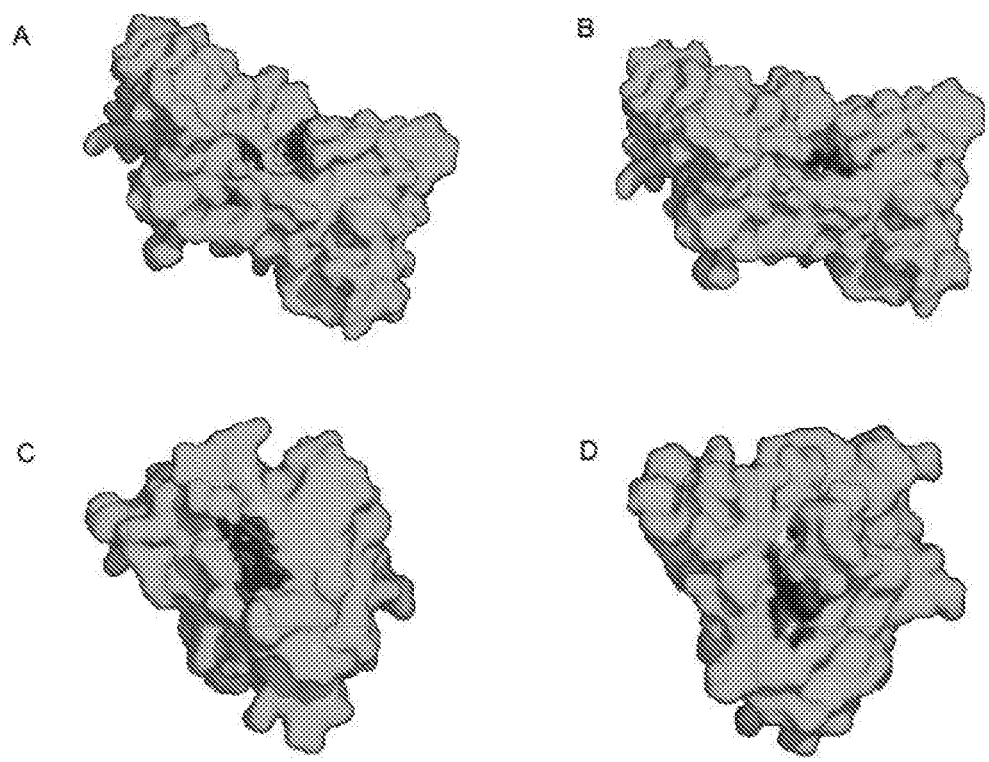
FIG. 10 shows putative Hsp70 binding sites in SOD1—4-5 hydrophobic residues flanked by basic residues. A) SOD1 dimer with N-terminal binding site shown in dark grey (residues 4-8), B) SOD1 dimer with C-terminal binding site shown in dark grey (residues 144-151). C) SOD1 monomer with N-terminal binding site shown in dark grey. D) SOD1 monomer with C-terminal binding site shown in dark grey.

Monomer/misfolded SOD1 was found to accumulate predominantly in motor neurons, prior to neurodegeneration whereas natively folded wild-type and mutant SOD1 is ubiquitous and found in all cell types. This observation, coupled with the demonstration that varying the expression level of mutant SOD1 in motor neurons alters the initiation and early progression of disease in transgenic mice[48], confirms neuronal toxicity of misfolded SOD1. The apparent decrease in SEDI-labeling at disease end stage is attributed to neuron loss, the primary site where misfolded SOD1 is generated. The accumulation of misfolded SOD1 in motor neurons may signal an insufficiency in cellular clearance mechanisms, the requirement of some chemical modification over time of SOD1 that triggers misfolding, or possibly a combination thereof. The observed selectivity of monomer/misfolded SOD1 deposition implies that there may be convergence of these risk factors. Exposure of the dimer interface epitope reveals sites of potential de novo protein-protein interactions, including the two putative Hsp70 binding sites[27] in the SOD1 sequence (FIG. 10). Motor neurons may be selectively vulnerable because of their inability to efficiently upregulate protein chaperones[4]. However, the levels of misfolded SOD1 observed make up only a minute fraction of total mutant SOD1 present. Comparable amounts of misfolded SOD1 accumulate in a mouse expressing an SOD1 truncation mutant; this is sufficient to cause an ALS-phenotype[28]. The age-related accumulation of misfolded SOD1 could also be attributed to age associated accumulation of oxidative insults by SOD1. A role of oxidation in SOD1 misfolding is supported by the finding that decreasing glutamate excitotoxicity related oxidative stress can protect mice from mutant SOD1-related toxicity[29, 30]. The observations that misfolded SOD1 is predominantly in motor neurons does not preclude a non-cell autonomous mechanism in SOD1-ALS[31], because other cell-types may influence motor neuron viability.

Figure 11:
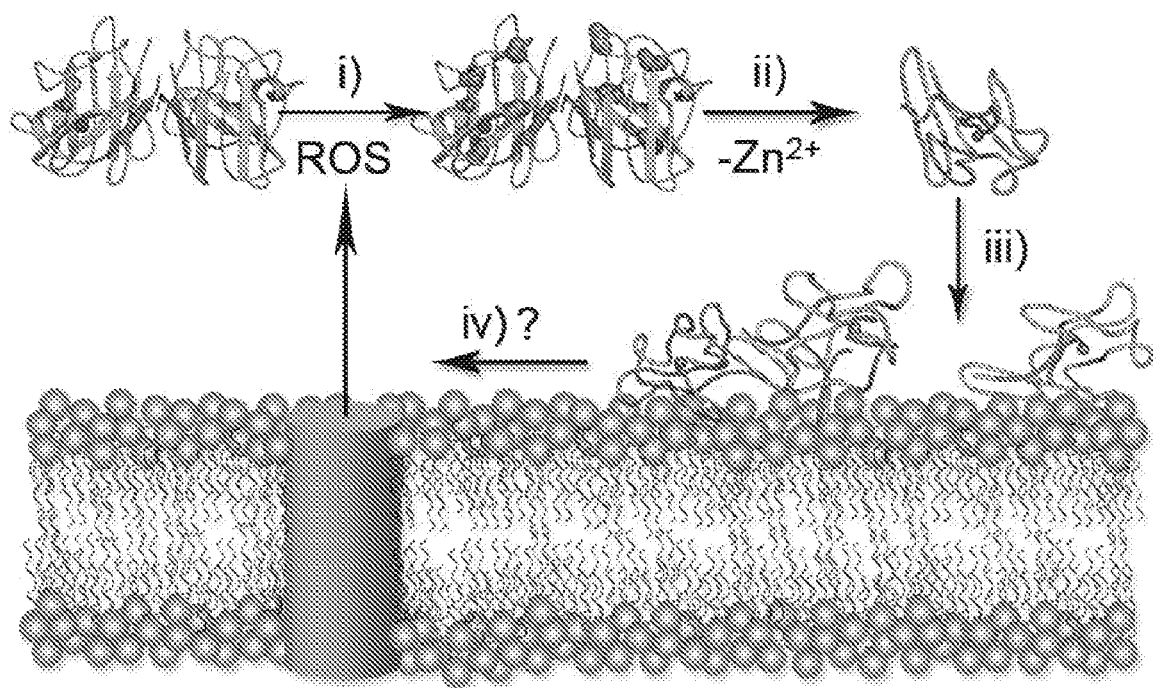
FIG. 11 shows a model of SOD1 misfolding pathway: i) oxidation of residues in native dimeric SOD1 from reactive oxygen species (ROS) produced in the mitochondria causes a loss of metal binding (ii). Zinc deficient SOD1 becomes misfolded and may oligomerize and bind to the mitochondrial outer membrane (iii). iv) Deposition of misfolded SOD1 on the mitochondria may reduce the efficiency of respiration[38], causing a higher turnover of the oxidative phosphorylation system and a net increase in ROS generation.
Figure 12:
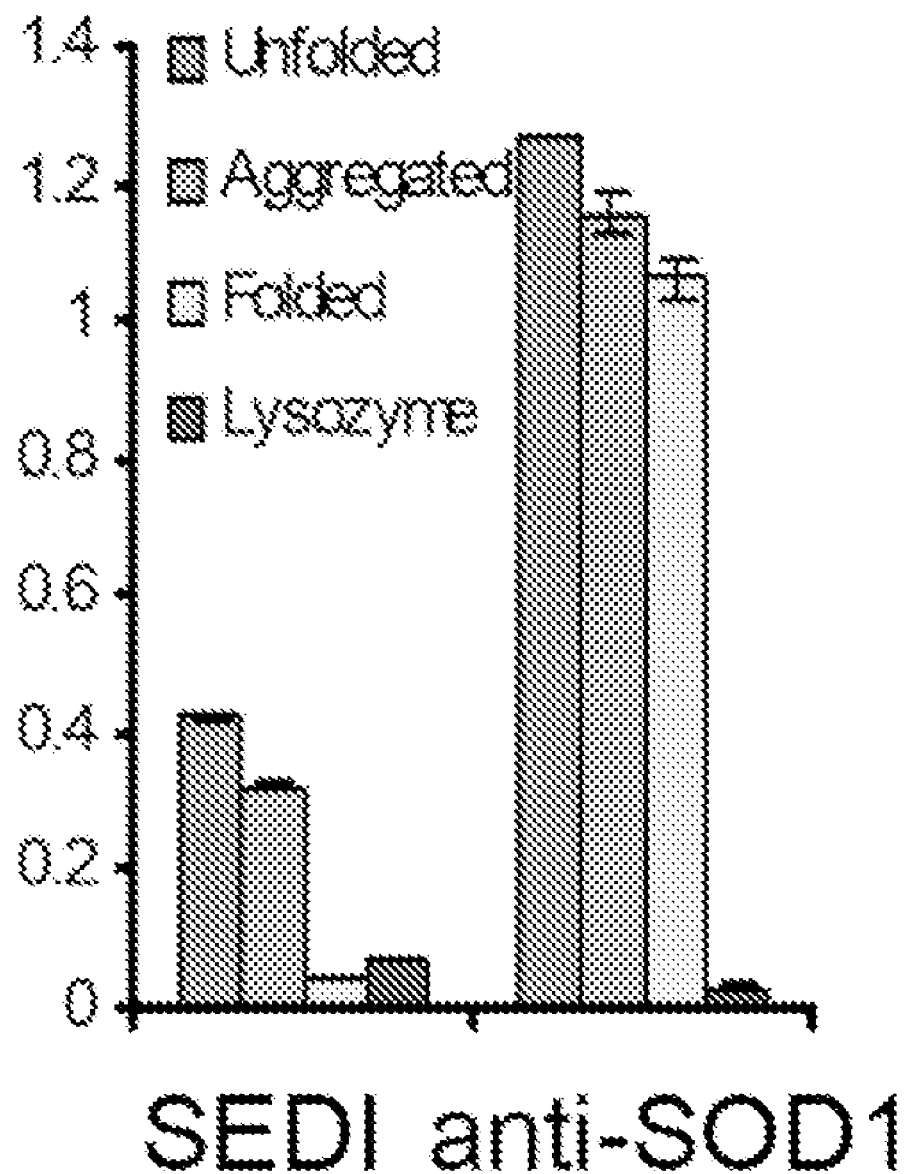
FIG. 12 shows the results of an enzyme linked immunosorbent assay (ELISA) comparing the reactivity of the SEDI antibody and a non-discriminating SOD1 antibody. SEDI reacts with unfolded or aggregated SOD1, but not folded SOD1. The non-discriminating antibody reacts with all forms of SOD1.

Immunohistological analysis using the SEDI antibody allowed the identification of vacuolated mitochondria within motor neurons as the primary deposition site of monomer/misfolded SOD1. Mitochondrial dysfunction has previously been implicated in ALS, and is an active area of research[32]. Severe mitochondrial pathology is observed in G93A and G37R-SOD1 transgenic mice[17, 18], mitochondrial abnormalities have been found in human cases of ALS[33, 34], and other groups have demonstrated that mutant SOD1 can deposit on mitochondria[7, 8, 22]. However, even in healthy non-transgenic rats, endogenous SOD1 has been found in association with mitochondria[35]. Furthermore, transgenic mice that overexpress human wild-type SOD1 also show mitochondrial co-localization[36]. Thus, the role of mutant SOD1 association with mitochondria has been unclear until now. By clearly demonstrating that at least a subset of mutant SOD1 associated with mitochondria is misfolded, these results provide a direct link between mutant SOD1 misfolding and mitochondrial degeneration in ALS. This deposition of misfolded SOD1 may be responsible for observed alterations in the oxidative phosphorylation efficiency of mitochondria[37, 38]. It is hypothesized that because SOD1 is an extremely stably folded protein, it may require chemical modification to promote misfolding[12]. The observations that misfolded SOD1 is concentrated around mitochondria, the principle source of oxidative stress in vivo, in conjunction with previous observations that SOD1 can become oxidized in ALS mice[39] and oxidative stress causes SOD1 misfolding in vitro[12], suggests oxidative insults may cause SOD1 misfolding in vivo (FIG. 11). Misfolded SOD1 deposition on mitochondria may itself lead to mitochondrial dysfunction and increased generation of oxygen radicals. Thus, a feedback loop may be created where SOD1 becomes misfolded as a result of oxidative modification, which then causes mitochondrial dysfunction that leads to greater oxidative stress (FIG. 11). Observed high levels of misfolded SOD1 in motor axons is consistent with our hypothesis that SOD1 misfolds as a result of its longer life-time in axons compared to that in the perikaryon, which allows for the accumulation of age-related chemical modifications such as oxidation[12]. Since vacuolated mitochondria with misfolded SOD1 are present within ALS-motor axons, these dilated structures may interfere with axonal transport in motor neurons. Thus, SOD1-ALS may arise from mitochondrial vacuolization, alterations in axonal transport or some combination of these two factors resulting as a consequence of SOD1 misfolding.

Since co-expression of wild-type SOD1 with mutant SOD1 results in earlier disease onset[21], and small amounts of misfolded SOD1 are observed in the wild-type SOD1 overexpressing mouse (FIG. 3F), the combined misfolding of wild-type and mutant SOD1 may account for earlier onset of symptoms in the mouse co-expressing wild-type and mutant SOD1. Disease onset and duration is also directly correlated to the expression level of mutant SOD1[40]. Furthermore, Borchelt and co-workers have found that levels of detergent insoluble SOD1 correlate with disease severity in SOD1-transgenic mice[5]. The greater amounts of monomer/misfolded SOD1 immunoprecipitated with the SEDI antibody (FIG. 1H) from the G93A-SOD1 mouse line (1Gur line[17]) than the G37R-SOD1 mouse[18] correlate with earlier onset of symptoms in the G93A mouse (~100 days) when compared to the G37R mouse (9 months). The total load of misfolded SOD1 may then be the true predictor of disease onset in human-SOD1 transgenic animals.

The SEDI antibody may have utility in drug discovery efforts aimed at identifying molecules that prevent SOD1 misfolding by stabilizing native SOD1. SEDI antibody was used as a biochemical marker to follow the appearance and progression of disease in SOD1-mice. As such, it also has potential use in diagnosis in humans. The antibody provides a method to follow disease course using CSF or other samples during therapies. In addition, the SEDI antibody may have direct therapeutic benefit whereby passive immunization blocks aberrant interactions with misfolded SOD1. This new research tool should expand experimental possibilities within ALS research and thus will be made suitably available.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES
REFERRED TO IN THE SPECIFICATION

1. Bruijn, L. I., Miller, T. M. & Cleveland, D. W. Unraveling the mechanisms involved in motor neuron degeneration in ALS. Annu Rev Neurosci 27, 723-49 (2004).
2. Rosen, D. R. et al. Mutations in Cu/Zn superoxide dismutase gene are associated with familial amyotrophic lateral sclerosis. Nature 362, 59-62 (1993).
3. Wood, J. D., Beaujeux, T. P. & Shaw, P. J. Protein aggregation in motor neurone disorders. Neuropathol Appl Neurobiol 29, 529-45 (2003).
4. Batulan, Z. et al. High threshold for induction of the stress response in motor neurons is associated with failure to activate HSF1. J Neurosci 23, 5789-98 (2003).
5. Wang, J. et al. Somatodendritic accumulation of misfolded SOD1-L126Z in motor neurons mediates degeneration: alphaB-crystallin modulates aggregation. Hum Mol Genet. 14, 2335-47 (2005).
6. Urushitani, M., Kurisu, J., Tsukita, K. & Takahashi, R. Proteasomal inhibition by misfolded mutant superoxide dismutase 1 induces selective motor neuron death in familial amyotrophic lateral sclerosis. J Neurochem 83, 1030-42 (2002).
7. Liu, J. et al. Toxicity of familial ALS-linked SOD1 mutants from selective recruitment to spinal mitochondria. Neuron 43, 5-17 (2004).
8. Pasinelli, P. et al. Amyotrophic lateral sclerosis-associated SOD1 mutant proteins bind and aggregate with Bcl-2 in spinal cord mitochondria. Neuron 43, 19-30 (2004).
9. Beckman, J. S., Carson, M., Smith, C. D. & Koppenol, W. H. ALS, SOD and peroxynitrite. Nature 364, 584 (1993).
10. Crow, J. P., Sampson, J. B., Zhuang, Y., Thompson, J. A. & Beckman, J. S. Decreased zinc affinity of amyotrophic lateral sclerosis-associated superoxide dismutase mutants leads to enhanced catalysis of tyrosine nitration by peroxynitrite. J Neurochem 69, 1936-44 (1997).
11. Forman, H. J. & Fridovich, I. On the stability of bovine superoxide dismutase. The effects of metals. J Biol Chem 248, 2645-9 (1973).
12. Rakhit, R. et al. Oxidation-induced misfolding and aggregation of superoxide dismutase and its implications for amyotrophic lateral sclerosis. J Biol Chem 277, 47551-6 (2002).
13. Rakhit, R. et al. Monomeric Cu,Zn-superoxide dismutase is a common misfolding intermediate in the oxidation models of sporadic and familial amyotrophic lateral sclerosis. J Biol Chem 279, 15499-504 (2004).
14. Kayed, R. et al. Common structure of soluble amyloid oligomers implies common mechanism of pathogenesis. Science 300, 486-9 (2003).
15. Paramithiotis, E. et al. A prion protein epitope selective for the pathologically misfolded conformation. Nat Med 9, 893-9 (2003).
16. Deng, H. X. et al. Amyotrophic lateral sclerosis and structural defects in Cu,Zn superoxide dismutase. Science 261, 1047-51 (1993).
17. Gurney, M. E. et al. Motor neuron degeneration in mice that express a human Cu,Zn superoxide dismutase mutation. Science 264, 1772-5 (1994).
18. Wong, P. C. et al. An adverse property of a familial ALS-linked SOD1 mutation causes motor neuron disease characterized by vacuolar degeneration of mitochondria. Neuron 14, 1105-16 (1995).
19. Bruijn, L. I. et al. Aggregation and motor neuron toxicity of an ALS-linked SOD1 mutant independent from wild-type SOD1. Science 281, 1851-4 (1998).
20. Furukawa, Y., Torres, A. S. & O'Halloran, T. V. Oxygen-induced maturation of SOD1: a key role for disulfide formation by the copper chaperone CCS. Embo J 23, 2872-81 (2004).
21. Jaarsma, D. et al. Human Cu/Zn superoxide dismutase (SOD1) overexpression in mice causes mitochondrial vacuolization, axonal degeneration, and premature motoneuron death and accelerates motoneuron disease in mice expressing a familial amyotrophic lateral sclerosis mutant SOD1. Neurobiol Dis 7, 623-43 (2000).
22. Higgins, C. M., Jung, C. & Xu, Z. ALS-associated mutant SOD1G93A causes mitochondrial vacuolation by expansion of the intermembrane space and by involvement of SOD1 aggregation and peroxisomes. BMC Neurosci 4, 16 (2003).
23. Feeney, S. J. et al. Presymptomatic motor neuron loss and reactive astrocytosis in the SOD1 mouse model of amyotrophic lateral sclerosis. Muscle Nerve 24, 1510-9 (2001).
24. Volles, M. J. & Lansbury, P. T., Jr. Zeroing in on the pathogenic form of alpha-synuclein and its mechanism of neurotoxicity in Parkinson's disease. Biochemistry 42, 7871-8 (2003).
25. Lambert, M. P. et al. Diffusible, nonfibrillar ligands derived from Abeta1-42 are potent central nervous system neurotoxins. Proc Natl Acad Sci USA 95, 6448-53 (1998).
26. Walsh, D. M. et al. Naturally secreted oligomers of amyloid beta protein potently inhibit hippocampal long-term potentiation in vivo. Nature 416, 535-9 (2002).
27. Rudiger, S., Germeroth, L., Schneider-Mergener, J. & Bukau, B. Substrate specificity of the DnaK chaperone determined by screening cellulose-bound peptide libraries. Embo J 16, 1501-7 (1997).

28. Jonsson, P. A. et al. Minute quantities of misfolded mutant superoxide dismutase-1 cause amyotrophic lateral sclerosis. Brain 127, 73-88 (2004).
29. Tateno, M. et al. Calcium-permeable AMPA receptors promote misfolding of mutant SOD1 protein and development of amyotrophic lateral sclerosis in a transgenic mouse model. Hum Mol Genet. 13, 2183-96 (2004).
30. Rothstein, J. D. et al. Beta-lactam antibiotics offer neuroprotection by increasing glutamate transporter expression. Nature 433, 73-7 (2005).
31. Clement, A. M. et al. Wild-type nonneuronal cells extend survival of SOD1 mutant motor neurons in ALS mice. Science 302, 113-7 (2003).
32. Manfredi, G. & Xu, Z. Mitochondrial dysfunction and its role in motor neuron degeneration in ALS. Mitochondrion 5, 77-87 (2005).
33. Bowling, A. C., Schulz, J. B., Brown, R. H., Jr. & Beal, M. F. Superoxide dismutase activity, oxidative damage, and mitochondrial energy metabolism in familial and sporadic amyotrophic lateral sclerosis. J Neurochem 61, 2322-5 (1993).
34. Chung, M. J. & Suh, Y. L. Ultrastructural changes of mitochondria in the skeletal muscle of patients with amyotrophic lateral sclerosis. Ultrastruct Pathol 26, 3-7 (2002).
35. Okado-Matsumoto, A. & Fridovich, I. Subcellular distribution of superoxide dismutases (SOD) in rat liver: Cu,Zn-SOD in mitochondria. Biol Chem 276, 38388-93 (2001).
36. Higgins, C. M., Jung, C., Ding, H. & Xu, Z. Mutant Cu, Zn superoxide dismutase that causes motoneuron degeneration is present in mitochondria in the CNS. J Neurosci 22, RC215 (2002).
37. Browne, S. E. et al. Metabolic dysfunction in familial, but not sporadic, amyotrophic lateral sclerosis. J Neurochem 71, 281-7 (1998).
38. Mattiazzi, M. et al. Mutated human SOD1 causes dysfunction of oxidative phosphorylation in mitochondria of transgenic mice. J Biol Chem 277, 29626-33 (2002).
39. Andrus, P. K., Fleck, T. J., Gurney, M. E. & Hall, E. D. Protein oxidative damage in a transgenic mouse model of familial amyotrophic lateral sclerosis. J Neurochem 71, 2041-8 (1998).
40. Dal Canto, M. C. & Gurney, M. E. A low expressor line of transgenic mice carrying a mutant human Cu,Zn superoxide dismutase (SOD1) gene develops pathological changes that most closely resemble those in human amyotrophic lateral sclerosis. Acta Neuropathol (Berl) 93, 537-50 (1997).
41. T. Siddique, A. Hentati, Clin Neurosci 3, 338 (1995).
42. Borchelt, D. R. et al. Superoxide dismutase 1 with mutations linked to familial amyotrophic lateral sclerosis possesses significant activity. Proc Natl Acad Sci USA 91, 8292-6 (1994).
43. Tiwari, A., Xu, Z. & Hayward, L. J. Aberrantly increased hydrophobicity shared by mutants of Cu,Zn-superoxide dismutase in familial amyotrophic lateral sclerosis. J Biol Chem 280, 29771-9 (2005).
44. Jonsson, P. A. et al. Minute quantities of misfolded mutant superoxide dismutase-1 cause amyotrophic lateral sclerosis. Brain 127, 73-88 (2004) 45. Liu, J., Lillo, C., Jonsson, P. A., Vande Velde, C., Ward, C. M., Miller, T. M., Subramaniam, J. R., Rothstein, J. D., Marklund, S., Andersen, P. M., Brannstrom, T., Gredal, O., Wong, P. C., Williams, D. S., and Cleveland, D. W. (2004). Toxicity of Familial ALS-Linked SOD1 Mutants from Selective Recruitment to Spinal Mitochondria. Neuron 43, 5-17.
46. Kikuchi, H. et al. Spinal cord endoplasmic reticulum stress associated with a microsomal accumulation of mutant superoxide dismutase-1 in an ALS model. Proceedings Of The National Academy Of Sciences Of The United States Of America 103, 6025-6030 (2006).
47. Atkin, J. D. et al. Induction of the unfolded protein response in familial amyotrophic lateral sclerosis and association of protein disulfide isomerase with superoxide dismutase 1. J Biol Chem (2006).
48. Boillee, S. et al. Onset and Progression in Inherited ALS Determined by Motor Neurons and Microglia. Science 312, 1389-92 (2006).
49. Bruijn, L. I., Becher, M. W., Lee, M. K., Anderson, K. L., Jenkins, N. A., Copeland, N. G., Sisodia, S. S., Rothstein, J. D., Borchelt, D. R., Price, D. L., and Cleveland, D. W. (1997). ALS-linked SOD1 mutant G85R mediates damage to astrocytes and promotes rapidly progressive disease with SOD1-containing inclusions. Neuron 18, 327-338.
50. Thompson, J D, Higgins D G, Gibson T J, 1994, Nucleic Acids Res. 22(22): 4673-4680.
51. Henikoff S. and Henikoff J. G., 1992, Proc. Natl. Acad. Sci. USA 89: 10915-10919.
52. Needleman and Wunsch. J. Mol. Biol., 1970, 48:443.
53. Smith and Waterman. Adv. Appl. Math. 1981, 2:482.
54. Carillo and Lipton SIAM J. Applied Math. 1988, 48:1073.
55. Computational Molecular Biology, Lesk, e.d. Oxford University Press, New York, 1988, Biocomputing: Informatics and Genomics Projects.
56. Devereux et al., Nucleic Acids Res., 1984, 12:387.
57. Altschul et al., J. Molec. Biol., 1990: 215:403.

We claim:

1. A method of detecting or monitoring familial amyotrophic lateral sclerosis in a subject having or suspected of having amyotrophic lateral sclerosis, comprising contacting a sample comprising motor neuron cells from the subject with an antibody or binding fragment thereof that binds to SEQ ID NO:1 in misfolded or monomeric SOD1, wherein familial amyotrophic lateral sclerosis is indicated if the antibody or binding fragment thereof binds to SEQ ID NO:1 in a misfolded or monomeric SOD1 in the sample.

2. The method according to claim 1, wherein the sample comprises cerebrospinal fluid, spinal cord tissue, brain cells, a portion of the dorsal horn.

3. The method of claim 2 wherein the sample comprises a mitochondrial and/or microsomal enriched fraction.

4. The method according to claim 1, wherein flow cytometry, Western blot, ELISA, or immunoprecipitation followed by SDS-PAGE immunocytochemistry is used to detect binding of the antibody or binding fragment thereof to misfolded or monomeric SOD1.

5. The method according to claim 1, wherein the antibody or binding fragment thereof binds to an epitope on the dimer interface of SOD1.

6. The method according to claim 1, wherein the antibody or binding fragment thereof is an antibody.

7. The method according to claim 6, wherein the antibody is a monoclonal antibody.

8. The method according to claim 1, wherein the antibody or binding fragment thereof is labeled with a detectable marker.

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Epitope

<400> SEQUENCE: 1

Ala Cys Gly Val Ile Gly Ile
1               5
```

-continued

```
<210> SEQ ID NO 2
<211> LENGTH: 9
<212> TYPE: PRT
<213> ORGANISM: Artificial Sequence
<220> FEATURE:
<223> OTHER INFORMATION: Epitope

<400> SEQUENCE: 2

Arg Leu Ala Cys Gly Val Ile Gly Ile
1               5

<210> SEQ ID NO 3
<211> LENGTH: 14
<212> TYPE: PRT
<213> ORGANISM: Artificial Sequence
<220> FEATURE:
<223> OTHER INFORMATION: Epitope

<400> SEQUENCE: 3

Gly Gly Arg Leu Ala Cys Gly Val Ile Gly Ile Gly Gly Lys
1               5                   10
```